United States Patent
Yoshioka et al.

(10) Patent No.: US 7,615,911 B2
(45) Date of Patent: Nov. 10, 2009

(54) FLIGHT STATE DETECTION APPARATUS OF MICRO OBJECT AND FLIGHT STATE DETECTION METHOD OF MICRO OBJECT

(75) Inventors: Kunihiko Yoshioka, Nagoya (JP); Takao Ohnishi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 526 days.

(21) Appl. No.: 11/444,276

(22) Filed: May 31, 2006

(65) Prior Publication Data

US 2006/0274514 A1    Dec. 7, 2006

(30) Foreign Application Priority Data

May 31, 2005    (JP)    ............... 2005-159799

(51) Int. Cl.
*H01L 41/08*    (2006.01)

(52) U.S. Cl. ...................... 310/321; 310/322

(58) Field of Classification Search ................ 310/321, 310/322, 328, 330, 331
See application file for complete search history.

(56) References Cited

U.S. PATENT DOCUMENTS

| | | | | |
|---|---|---|---|---|
| 4,114,063 A | * | 9/1978 | Nelkin et al. | 310/334 |
| 4,131,815 A | | 12/1978 | Boatright | |
| 4,193,010 A | * | 3/1980 | Kompanek | 310/330 |
| 4,540,981 A | * | 9/1985 | Lapetina et al. | 340/618 |
| 4,904,894 A | * | 2/1990 | Henry et al. | 310/328 |
| 4,976,156 A | * | 12/1990 | Lew | 73/861.24 |
| 5,932,953 A | * | 8/1999 | Drees et al. | 310/324 |
| 6,601,464 B1 | | 8/2003 | Downing, Jr. | |
| 6,852,524 B2 | * | 2/2005 | Okamura et al. | 435/287.1 |
| 6,989,625 B2 | * | 1/2006 | Suzuki et al. | 310/334 |
| 7,467,558 B2 | * | 12/2008 | Fukuda et al. | 73/862.68 |

FOREIGN PATENT DOCUMENTS

| | | |
|---|---|---|
| EP | 0 325 386 A1 | 7/1989 |
| EP | 0 766 086 A2 | 4/1997 |
| JP | 2000-180250 | 6/2000 |
| JP | 2001-124789 | 5/2001 |
| JP | 2001-186881 | 7/2001 |

* cited by examiner

*Primary Examiner*—Mark Budd
(74) *Attorney, Agent, or Firm*—Burr & Brown

(57) ABSTRACT

Disclosed herein is a flight state detection apparatus and a flight state detection method that is capable of accurately detecting the flight state of a micro object ejected from a micro object ejection part. The flight state detection apparatus is constructed in a simplified structure and is manufactured at low costs. The flight state detection apparatus includes a sensor substrate, a piezoelectric/electrostrictive element, and an aperture plate. The sensor substrate includes a thick support part and a vibrating plate supported by the thick support part in a cantilever shape. The piezoelectric/electrostrictive element is mounted to a fixed end side of the vibrating plate. In the aperture plate, an aperture is formed, which is opposite to a target part disposed at a free end side of the vibrating plate. When the micro object passes through the aperture, and then collides with the target part, the vibrating plate is vibrated, and an electromotive force corresponding to the vibration state is generated in the piezoelectric/electrostrictive element.

61 Claims, 20 Drawing Sheets

FLIGHT STATE DETECTION APPARATUS OF MICRO OBJECT AND FLIGHT STATE DETECTION METHOD OF MICRO OBJECT

BACKGROUND OF THE INVENTION

1. Field of the Invention

The present invention relates to a flight state detection apparatus and a flight state detection method that is capable of detecting the flight state of a micro object in flight.

2. Description of the Related Art

For example, various methods of manufacturing a so-called DNA chip (a DNA micro array) are well known. The DNA chip is generally constructed by arraying and fixing micro spots of several thousand to ten thousand or more kinds of different DNA pieces on a substrate, such as microscope slide glass, with high density.

As examples of the DNA chip manufacturing methods, there have been proposed methods of manufacturing a DNA chip using a micropipette for ejecting drops having micro volume (for example, see the following Patent References 1 and 2). The micropipette includes an injection port for injecting a sample solution from the outside, a cavity for allowing the sample solution injected from the injection port to be filled therein, an ejection port communicating with the cavity, and a piezoelectric/electrostrictive element constructed to change the interior volume of the cavity such that the sample solution can be ejected from the ejection port.

According to the above-described DNA chip manufacturing methods, the interior volume of the cavity is changed by the driving operation of the piezoelectric/electrostrictive element. As the interior volume of the cavity is changed, the sample solution moves from the cavity to the ejection port in the form of a streamline flow. That is, a predetermined amount of the sample solution is delivered from the cavity to the ejection port. As the predetermined amount of the sample solution is ejected from the ejection port, micro drops of the sample solution are generated. The micro drops of the sample solution ejected from the micropipette are attached to the substrate, and the micro drops are arrayed and fixed on the substrate as micro spots. In this way, the DNA chip is manufactured.

An apparatus constructed to eject a micro object (hereinafter, simply referred to as a "micro object ejection apparatus"), such as the micropipette used in the DNA chip manufacturing method as described above, may be utilized in various technical fields.

Furthermore, a mass sensor constructed to measure the mass of this kind of micro object has been proposed (for example, see the following Patent Reference 3). In the case that the micro object is attached to a vibrating plate, on which the piezoelectric/electrostrictive element is disposed, the mass sensor serves to measure the change of the resonant frequency of the vibrating plate, which is caused by the mass change of the vibrating plate due to the attachment of the micro object to the vibrating plate, whereby the mass change of the vibrating plate (i.e., the mass of the micro object) is measured.

[Patent Reference 1] Japanese Unexamined Patent Publication No. 2001-124789

[Patent Reference 2] Japanese Unexamined Patent Publication No. 2001-186881

[Patent Reference 3] Japanese Unexamined Patent Publication No. 2000-180250

In this kind of micro object ejection apparatus, the dried and hardened portion of the micro object or foreign matter may be attached around the ejection port, and, as a result, the ejection port may be obstructed. In this case, the micro object may not be accurately ejected toward a predetermined position to which the micro object is to be ejected (for example, see columns [0010] and [0019] of Patent Reference 1).

Also, the detection of the flight state of the micro object using the mass sensor as described in Patent Reference 3 may only be applied to a micro object which is attached to the vibrating plate during a certain period of time (a period of time that the change of the resonant frequency can be measured). Furthermore, in the detection of the flight state using the mass sensor, when the micro object is intermittently ejected from the same micro object ejection apparatus by predetermined periods, it is difficult to continuously detect the flight state of the micro object using the same mass sensor.

SUMMARY OF THE INVENTION

Therefore, the present invention has been made in view of the above problems, and it is an object of the present invention to provide a flight state detection apparatus and a flight state detection method that is capable of accurately detecting the flight state of a micro object ejected from the micro object ejection apparatus (the ejection state of the micro object ejection apparatus), the flight state detection apparatus being manufactured in a simplified structure and at low costs.

(A) In accordance with one aspect of the present invention, a flight state detection apparatus of a micro object (hereinafter, simply referred to as a "flight state detection apparatus") including the following constructions for detecting the flight state of the micro object in flight.

(A01) The flight state detection apparatus according to the present invention includes: a vibration generating part; and at least one piezoelectric/electrostrictive element constructed to convert vibration generated in the vibration generating part into an electric signal. The vibration generating part has at least one target part, with which the micro object collides, and is constructed such that the vibration is generated in the vibration generating part by the collision of the micro object with the target part.

In the flight state detection apparatus with the above-described construction according to the present invention, when the micro object in flight collides with the target part, the vibration generating part is vibrated. The vibration is converted into an electric signal by the piezoelectric/electrostrictive element. The flight state of the micro object is detected based on the electric signal.

(A02) In the above-described construction A01, plurality of the target parts may be mounted to the single vibration generating part. For example, the flight state detection apparatus may be controlled such that plural micro objects, the number of which is the same as the number of the plural target parts, can simultaneously collide with the plural target parts, whereby the flight state of the micro objects which are flying along predetermined flight routes of the respective micro objects, is simultaneously detected. Consequently, the time necessary for the flight state detection is reduced. Also, the circuit construction for the flight state detection is simplified.

(A03) In the above-described construction A01 or A02, plurality of the piezoelectric/electrostrictive elements may be electrically connected with each other. According to this construction, electric signals are generated in the plural piezoelectric/electrostrictive elements by the one-time collision of the micro objects with the target parts, and the electric signals are added up. As a result, the sensitivity of the flight state detection apparatus is improved. Consequently, according to this construction, it is possible to accurately perform the flight state detection of a micro object having smaller mass.

Also, according to this construction, electric signals are generated in the plural piezoelectric/electrostrictive elements by the one-time collision of the micro objects with the target parts, and the electric signals are compared with each other. For example, vibration of a specific mode (a bending mode or a twisting mode) may be generated in the vibration generating part depending upon the collision state between the micro objects and the target parts. The vibration mode may be determined by comparing the electric signals generated in the respective piezoelectric/electrostrictive elements with each other. Consequently, it is possible to detect various flight states of the micro objects. For example, it is possible not only to determine whether the micro objects are in flight but also to determine whether the micro objects have deviated from the predetermined flight routes.

The electrical connection between the plural piezoelectric/electrostrictive elements may be accomplished in a directly connecting manner or via an operation/control circuit. Especially, in the case that the electrical connection between the plural piezoelectric/electrostrictive elements is accomplished in the directly connecting manner, the comparison between the outputs of the piezoelectric/electrostrictive elements is performed by the connection circuit of the piezoelectric/electrostrictive elements. Consequently, the construction of the operation/control circuit is simplified, and the determination of the micro object is simply performed.

(A04) In any one of the above-described constructions A01 to A03, the flight state detection apparatus may further include: a coating layer formed at a surface of the target part. Consequently, it is possible to inhibit the change in the vibration characteristics of the vibration generating part due to the micro object remaining on the target part. Also, in the case that the micro object is liquid, foreign matters (such as dusts) from the atmosphere attach around the target part, whereby the contamination of the target part is effectively prevented.

(A05) In any one of the above-described constructions A01 to A04, the flight state detection apparatus may further include a drive part for generating a drive voltage necessary to drive the piezoelectric/electrostrictive element. The piezoelectric/electrostrictive element is driven by the drive part, and therefore, the vibration generating part is forcibly and externally vibrated. Due to this forced vibration of the vibration generating part, for example, the material object attached to the target part (such as the residual substance of the micro object or foreign matter) can be removed. Alternatively, it is possible to acquire the change of the resonant frequency in the vibration generating part based on the vibration state when the vibration generating part is forcibly vibrated.

(A06) In the above-described construction A05, the flight state detection apparatus may further include a resonant frequency acquisition part for acquiring a resonant frequency of the vibration generating part, and the drive part may be constructed such that the drive part drives the piezoelectric/electrostrictive element based on the resonant frequency acquired by the resonant frequency acquisition part.

In this construction, for example, the vibration generating part is forcibly vibrated, for example, by the application of a drive voltage from the drive part. (The drive voltage of this case may include, for example, a DC voltage, an AC voltage of the resonant frequency previously acquired, an alternating voltage of a specific frequency having a predetermined level, etc.) Based on this vibration, the resonant frequency acquisition part acquires the resonant frequency of the vibration generating part. When the vibration generating part is forcibly vibrated by the drive part next time, the drive part drives the vibration generating part based on this acquired resonant frequency.

According to this construction, it is possible to efficiently remove the material object attached to the target part. Alternatively, it is possible to detect the abnormality of the flight state detection apparatus (for example, damage to the vibration generating part or excessive attachment of the material object to the target part).

(A07) In the above-described construction A06, the resonant frequency acquisition part may be constructed such that the resonant frequency acquisition part acquires the resonant frequency after output of the drive voltage from the drive part is interrupted.

According to this construction, for example, it is possible to acquire the resonant frequency as follows. First, a DC voltage is applied to the piezoelectric/electrostrictive element for a predetermined period of time (a time sufficiently longer than a period corresponding to the expected resonant frequency), and then the application of the DC voltage is interrupted. As a result, free vibration with damping is generated in the piezoelectric/electrostrictive element. Due to this free vibration with damping, an AC voltage is generated in the piezoelectric/electrostrictive element. The frequency of the generated voltage is acquired by the resonant frequency acquisition part, whereby the resonant frequency of the vibration generating part is acquired.

(A08) In the above-described construction A06, the drive part may be constructed such that the drive part outputs the drive voltage with respect to some of the plural piezoelectric/electrostrictive elements, and the resonant frequency acquisition part may be constructed such that the resonant frequency acquisition part acquires the resonant frequency based on the electric signals from the other piezoelectric/electrostrictive elements than the piezoelectric/electrostrictive elements to which the drive voltage from the drive part is outputted.

According to this construction, the forced vibration of the vibration generating part by the drive part and the acquisition of the resonant frequency by the resonant frequency acquisition part can be carried out almost at the same time.

(A09) In any one of the above-described constructions A01 to A08, the flight state detection apparatus may further include a vibration mode determining part for determining a vibration mode of the vibration generating part based on the electric signal.

Specifically, vibration of a specific mode (a bending mode or a twisting mode) may be generated in the vibration generating part depending upon the collision state between the micro objects and the target parts. According to this construction, the vibration mode is determined by the vibration mode determining part. For example, it is possible to determine the vibration mode based on the amplitude of the electric signal generated by the piezoelectric/electrostrictive element. Alternatively, the vibration mode may be determined by comparing the electric signals generated in the respective piezoelectric/electrostrictive elements with each other. Otherwise, the plural piezoelectric/electrostrictive elements are electrically connected with each other, the electric signals are overlapped with each other, and the amplitude of the electric signals is acquired, whereby the determination of the vibration mode is accomplished.

According to this construction, it is possible to detect various flight states of the micro objects. For example, it is possible not only to determine whether the micro objects are in flight but also to determine whether the micro objects have deviated from the predetermined flight routes.

(A10) In any one of the above-described constructions A01 to A09, the vibration generating part may be constructed from a plate-shaped member having a longitudinal direction, the target part may be mounted at one end side of the plate-shaped member in the longitudinal direction of the plate-shaped member, and the piezoelectric/electrostrictive element may be fixedly mounted on a surface of the other end side of the plate-shaped member. In this case, the piezoelectric/electrostrictive element may be disposed onto the surface where the target part is mounted. Alternatively, the piezoelectric/electrostrictive element may be disposed onto the surface opposite to the side where the target part is mounted.

According to this construction, the distance between the target part and the piezoelectric/electrostrictive element may be set such that the distance between the target part and the piezoelectric/electrostrictive element is sufficiently large. Accordingly, a force from energy applied to the target part by the collision between the micro object and the target part is amplified according to leverage, and a large stress is generated in the piezoelectric/electrostrictive element. As a result, a relatively large electric signal is obtained at the piezoelectric/electrostrictive element. Consequently, the sensitivity of the flight state detection apparatus is improved, and it is possible to accurately perform the flight state detection of a micro object having smaller mass.

(A11) In the above-described construction A10, the plate-shaped member may be constructed such that the rigidity of the other end side of the plate-shaped member is lower than that of the one end side of the plate-shaped member.

According to this construction, when the micro object collides with the target part, stress is concentrated on the other end side of the plate-shaped member constituting the vibration generating part, the rigidity of which is low (the side where the piezoelectric/electrostrictive element is mounted). As a result, a large electric signal is obtained at the piezoelectric/electrostrictive element. Consequently, the sensitivity of the flight state detection apparatus is improved. Therefore, according to this construction, it is possible to accurately perform the flight state detection of a micro object having smaller mass.

(A12) In the above-described construction A10 or A11, the plural piezoelectric/electrostrictive elements may be fixedly mounted on one-side surface of the plate-shaped member and on a predetermined position of the other-side surface of the plate-shaped member, which is opposite to an inner part of the one-side surface of the plate-shaped member. In this case, the piezoelectric/electrostrictive elements mounted on one-side surface of the plate-shaped member and the piezoelectric/electrostrictive elements mounted on the other-side surface of the plate-shaped member are electrically connected with each other.

(A13) In any one of the above-described constructions A01 to A12, the flight state detection apparatus may further include: a micro object ejection part constructed to eject the micro object; and a control part for controlling the micro object ejection part. In this case, the control part controls the micro object ejection part such that the micro object can be ejected at a specific frequency approximate to 1/n times (n is a natural number) a resonant frequency of the vibration generating part.

According to this construction, the micro object is ejected by the micro object ejection part such that the micro object can be elected at the specific frequency approximate to 1/n times (n is a natural number) the resonant frequency of the vibration generating part. The ejected micro object intermittently collides with the target part by periods corresponding to the specific frequency. As a result, the vibration generating part is vibrated at the frequency approximately equal to the resonant frequency. Consequently, the vibration generating part is more efficiently vibrated, and the sensitivity of the flight state detection apparatus is improved.

(A14) In the above-described construction A13, the control part may be constructed such that the control part controls the micro object ejection part under the following condition.

On the assumption that the resonant frequency is f0 and the specific frequency is f1, $$(n-0.2)f1 \leq f0 \leq (n+0.25)f1 \text{ [n is a natural number]}.$$

According to this construction, the vibration generating part is more efficiently vibrated, and the sensitivity of the flight state detection apparatus is improved.

(A15) In the above-described construction A13 or A14, the control part may be constructed such that the control part controls the micro object ejection part under the following condition.

On the assumption that time necessary for the vibration generating part to absorb kinetic energy of the micro object when the micro object collides with the target part is T1, and an inherent period corresponding to the resonant frequency of the vibration generating part is T0, $$T1 \leq 0.2 \, T0,$$

For example, the structure (the material or the dimensions) of the vibration generating part may be set based on the flight velocity of the micro object and the state of the micro object (mass, volume, shape, whether the micro object is solid, fluid, or gas, etc.) such that the above-described relationships are satisfied.

According to this construction, the vibration generating part is more efficiently vibrated, and the sensitivity of the flight state detection apparatus is improved.

(A16) In any one of the above-described constructions A01 to A15, the flight state detection apparatus may further include a flat plate-shaped aperture plate intersecting the flight direction of the micro object, and the aperture plate may be provided with an aperture, which is a through-hole for allowing the micro object to pass therethrough. The aperture plate is located at an upper stream side than the target part in the flight direction of the micro object.

According to this construction, for example, when the micro drop ejected from the micro object ejection apparatus flies along a predetermined flight route in a flight direction, the aperture plate may be disposed such that the micro object can pass through the aperture. Consequently, it is possible to detect the deviation of the micro object from the flight route by the very simplified construction of the apparatus.

Also, according to this construction, the position of the aperture is appropriately set, and therefore, it is possible that only a predetermined vibration mode is selectively generated in the vibration generating part (C) In accordance with another aspect of the present invention, a flight state detection method of a micro object (hereinafter, simply referred to as a "flight state detection method") including the following steps for detecting the flight state of the micro object in flight.

(C01) The flight state detection method according to the present invention includes the following steps (s1) to (s4): (s1) ejecting the micro object from the micro object ejection part, (s2) forcing the ejected micro object to collide with a target part to vibrate a vibration generating part having the target part, (s3) converting the vibration of the vibration generating part into an electric signal using a piezoelectric/electrostrictive element, and (s4) detecting the flight state of the micro object based on the electric signal.

According to this method, in the case that the micro object is intermittently ejected from the same micro object ejection apparatus by predetermined periods, it is possible to continuously detect the flight state of the micro object using the same micro object ejection apparatus with ease.

(C02) In the flight state detection method according to the above-described paragraph C01, the step (s1) of ejecting the micro object may include ejecting the micro object at a specific frequency approximate to 1/n times (n is a natural number) a resonant frequency of the vibration generating part.

According to this method, the vibration generating part can be vibrated at the specific frequency approximately equal to 1/n times (n is a natural number) the resonant frequency at the step (s2) of vibrating the vibration generating part. Consequently, the vibration generating part is more efficiently vibrated, and the sensitivity of the flight state detection is improved by the step (s4) of detecting the flight state of the micro object.

(C03) In the flight state detection method according to the above-described paragraph C02, on the assumption that the resonant frequency is f0 and the specific frequency is f1, the step (s1) of ejecting the micro object may include ejecting the micro object at the specific frequency satisfying the following inequality:

$$(n-0.2)f1 \leq f0 \leq (n+0.25)f1 \text{ [n is a natural number]}.$$

According to this method, the vibration generating part is more efficiently vibrated at the step (s2) of vibrating the vibration generating part. Consequently, the sensitivity of the flight state detection is improved by the step (s4) of detecting the flight state of the micro object.

(C04) In the flight state detection method according to any one of the above-described paragraphs C01 to C03, on the assumption that time necessary for the vibration generating part to absorb kinetic energy of the micro object when the micro object collides with the target part is T1, and an inherent period corresponding to the resonant frequency of the vibration generating part is T0, the step (s1) of ejecting the micro object may include ejecting the micro object under the condition satisfying the following inequality:

$$T1 \leq 0.2 \, T0.$$

According to this method, the vibration generating part is more efficiently vibrated at the step (s2) of vibrating the vibration generating part, and the sensitivity of the flight state detection is improved by the step (s4) of detecting the flight state of the micro object.

(C05) In the flight state detection method according to any one of the above-described paragraphs C01 to C04, the step (s4) of detecting the flight state of the micro object may include determining a vibration mode of the vibration generating part based on the electric signal.

For example, it is possible to determine the vibration mode at the step (s4) based on the amplitude of an electric signal generated at the step (s3), which is the output of the piezoelectric/electrostrictive element. Alternatively, it is also possible to determine the vibration mode at the step (s4) by comparing electric signals, which are the outputs from plural piezoelectric/electrostrictive elements, at the step (s3). Otherwise, it may also be possible to determine the vibration mode at the step (s4) based on a signal obtained by overlapping the electric signals of the plural piezoelectric/electrostrictive elements.

According to this method, it is possible to detect various flight states of the micro object. For example, it is possible not only to determine whether the micro object is in flight but also to determine whether the micro object has deviated from a predetermined flight route.

(C06) In the flight state detection method according to the above-described paragraph C05, the step (s4) of detecting the flight state of the micro object may include determining the vibration mode of the vibration generating part based on electric signals outputted from a first piezoelectric/electrostrictive element and a second piezoelectric/electrostrictive element, which are electrically connected with each other.

In this case, the electric signals are outputted from the first piezoelectric/electrostrictive element and the second piezoelectric/electrostrictive element, which are electrically connected with each other, respectively, at the step (s3) of converting the vibration of the vibration generating part into the electric signal. At the step (s4), which follows the step (s3), the vibration mode of the vibration generating part is determined based on the respective electric signals from the first piezoelectric/electrostrictive element and the second piezoelectric/electrostrictive element.

According to this method, a specific vibration mode (a bending mode or a twisting mode) generated in the vibration generating part is determined depending upon the collision state between the micro object and the target part. Consequently, it is possible to detect various flight states of the micro object. For example, it is possible not only to determine whether the micro object is in flight but also to determine whether the micro object has deviated from the predetermined flight route.

Especially, in the case of using a circuit construction in which the plural piezoelectric/electrostrictive elements are directly electrically connected with each other, it is possible to perform the comparison between the outputs of the piezoelectric/electrostrictive elements by the connection circuit of the piezoelectric/electrostrictive elements. Consequently, the step (s4) of detecting the flight state of the micro object can be simply performed.

(C07) In the flight state detection method according to any one of the above-described paragraphs C01 to C06, the flight state detection method may further include the following steps of: (s11) acquiring the resonant frequency of the vibration generating part; and (s12) driving the piezoelectric/electrostrictive element(s) based on the acquired resonant frequency.

In this case, the step (s11) of acquiring the resonant frequency of the vibration generating part and the step (s12) of driving the piezoelectric/electrostrictive element(s) based on the acquired resonant frequency may be performed independently from the above-described steps (s1) to (s4). Specifically, the step (s11) of acquiring the resonant frequency of the vibration generating part and the step (s12) of driving the piezoelectric/electrostrictive element(s) based on the acquired resonant frequency is not necessarily carried out after the step (s4) of detecting the flight state of the micro object is carried out.

According to this method, it is possible to more efficiently remove a material object attached to the target part. Alternatively, it is possible to detect the abnormality of a flight state detection apparatus used to perform this method (for example, damage to the vibration generation part or excessive attachment of the material object to the target part).

(C08) In the flight state detection method according to the above-described paragraph C07, it is preferable that the step (s12) of acquiring the resonant frequency of the vibration generating part be carried out after the step (s11) of driving the piezoelectric/electrostrictive element(s) is completed.

According to this method, for example, the resonant frequency may be acquired as follows. First, a DC voltage is applied to the piezoelectric/electrostrictive element(s) for a predetermined period of time (a time sufficiently longer than an inherent period corresponding to the expected resonant frequency) at the step (s11), and then the application of the DC voltage is interrupted. As a result, free vibration with damping is generated in the piezoelectric/electrostrictive element(s). Due to this free vibration with damping, an AC voltage is generated in the piezoelectric/electrostrictive element(s). The frequency of the generated voltage is acquired at the step (s12), whereby the resonant frequency of the vibration generating part is acquired.

(C09) In the flight state detection method according to the above-described paragraph C07, the step (s11) of driving the piezoelectric/electrostrictive element(s) may include outputting the drive voltage with respect to some of the plural piezoelectric/electrostrictive elements, and the step (s12) of acquiring the resonant frequency of the vibration generating part may include acquiring the resonant frequency based on the electric signals from the other piezoelectric/electrostrictive elements than the piezoelectric/electrostrictive elements to which the drive voltage is outputted.

According to this method, the forced vibration of the vibration generating part by the drive part and the acquisition of the resonant frequency can be carried out almost at the same time.

(C10) In the flight state detection method according to any one of the above-described paragraphs C01 to C09, the step (s1) of ejecting the micro object may include forcing the micro object to collide with a predetermined position of the target part at a predetermined frequency to vibrate the vibration generating part in a predetermined vibration mode at the step (s2).

According to this method, vibration of the predetermined mode is selectively generated in the vibration generating part. Consequently, it is possible to detect various flight states of the micro object. For example, it is possible to accurately perform the flight state detection of a micro object having very small mass by selectively generating vibration of the primary bending mode in the vibration generating part.

BRIEF DESCRIPTION OF THE DRAWINGS

The above and other objects, features and other advantages of the present invention will be more clearly understood from the following detailed description taken in conjunction with the accompanying drawings in which:

FIG. 6A is a plan view of the dispensing apparatus, and FIG. 6B is a side view of the dispensing apparatus;

FIG. 9A is an enlarged side sectional view of the flight state detection apparatus, FIG. 9B is an enlarged plan view of the flight state detection apparatus, and FIG. 9C is an enlarged plan view of the flight state detection apparatus, the inner structure of which is exposed;

FIG. 10A is a side sectional view of the principal components of the flight state detection apparatus, FIG. 10B is a plan view of the principal components of the flight state detection apparatus, and FIG. 10C is a plan view illustrating an example of the construction for simultaneously detecting the flight state of plural micro objects;

FIG. 12A is a perspective view illustrating the vibration state of the vibrating plate in a bending mode, and FIG. 12B is a perspective view illustrating the vibration state of the vibrating plate in a twisting mode;

FIG. 13A is an enlarged plan view of the flight state detection apparatus, and FIG. 13B is an enlarged perspective view illustrating the vibration state of a vibrating plate;

DESCRIPTION OF THE PREFERRED EMBODIMENTS

Now, preferred embodiments of the present invention will be described in detail with reference to the accompanying drawings.

<Construction of DNA Chip>

Figure 1:
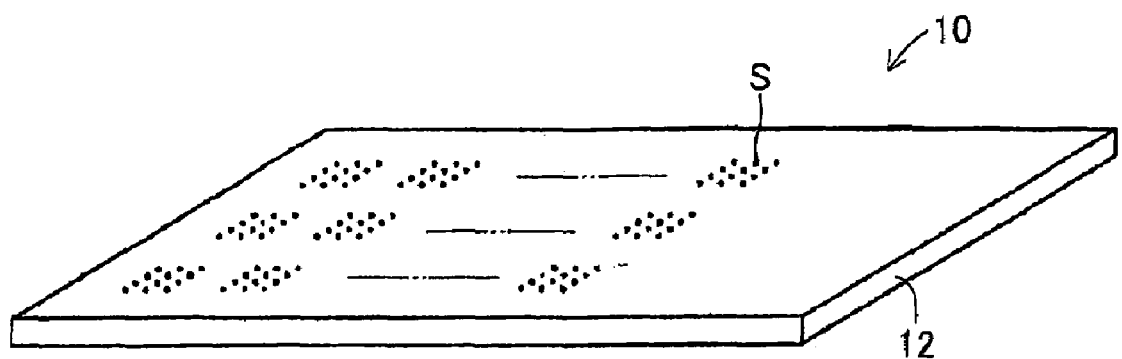
FIG. 1 is an external view (a perspective view) illustrating the general construction of a DNA chip.
Figure 2:
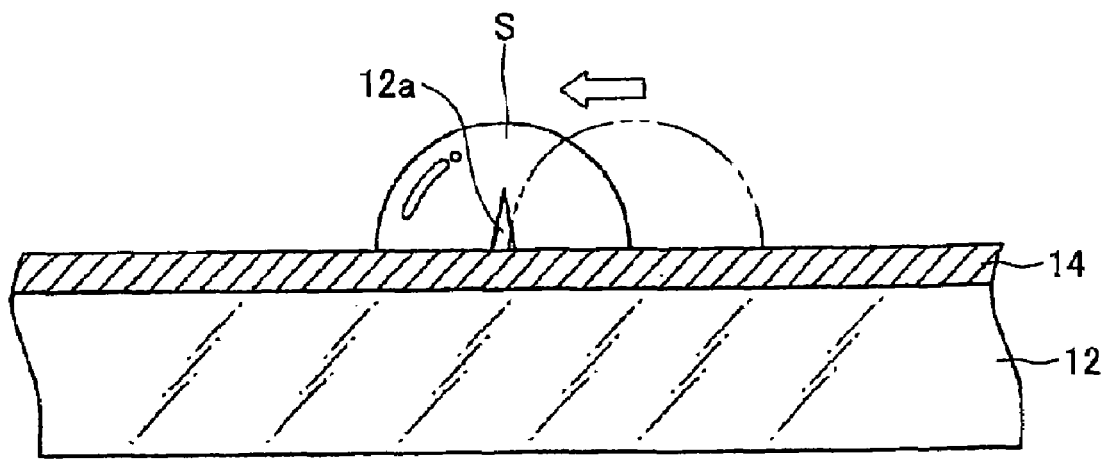
FIG. 2 is an enlarged sectional view of the DNA chip shown in FIG. 1.

FIG. 1 is an external view (a perspective view) illustrating the general construction of a DNA chip 10, and FIG. 2 is an enlarged sectional view of the DNA chip shown in FIG. 1.

As shown in FIG. 1, the DNA chip 10 is constructed by arranging plural micro spots S, which are formed by micro drops of a sample solution, on a DNA chip substrate 12, which is made of microscope slide glass.

As shown in FIG. 2, a protrusion 12a is formed on the DNA chip 12 at a predetermined position where the corresponding micro spot S is to be formed. When the corresponding micro spot S drops while deviating from the predetermined position, the protrusion 12a serves to compensate for the position deviation. Specifically, when a portion of the micro spot S is caught by the protrusion 12a (see a two-dot chain line), as shown in FIG. 2, the micro spot S is moved to the predetermined position by the surface tension of the micro spot S.

Also, a sample support layer 14, which is a poly-L-lysine layer having a hydrophilic property, is formed on the surface of the DNA chip substrate 12.

<Construction of Micropipette>

Figure 3:
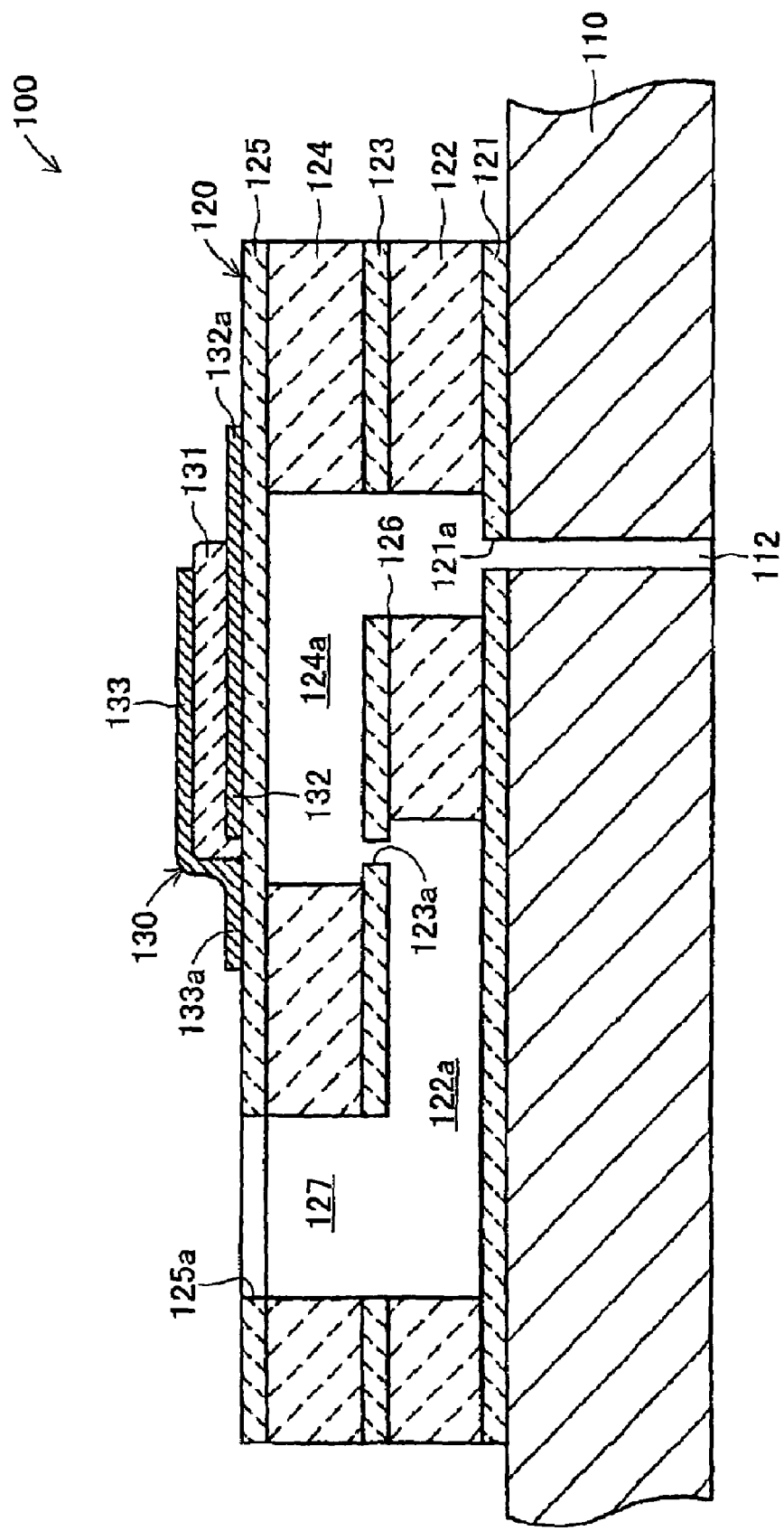
FIG. 3 is an enlarged sectional view of a micropipette.
Figure 4:
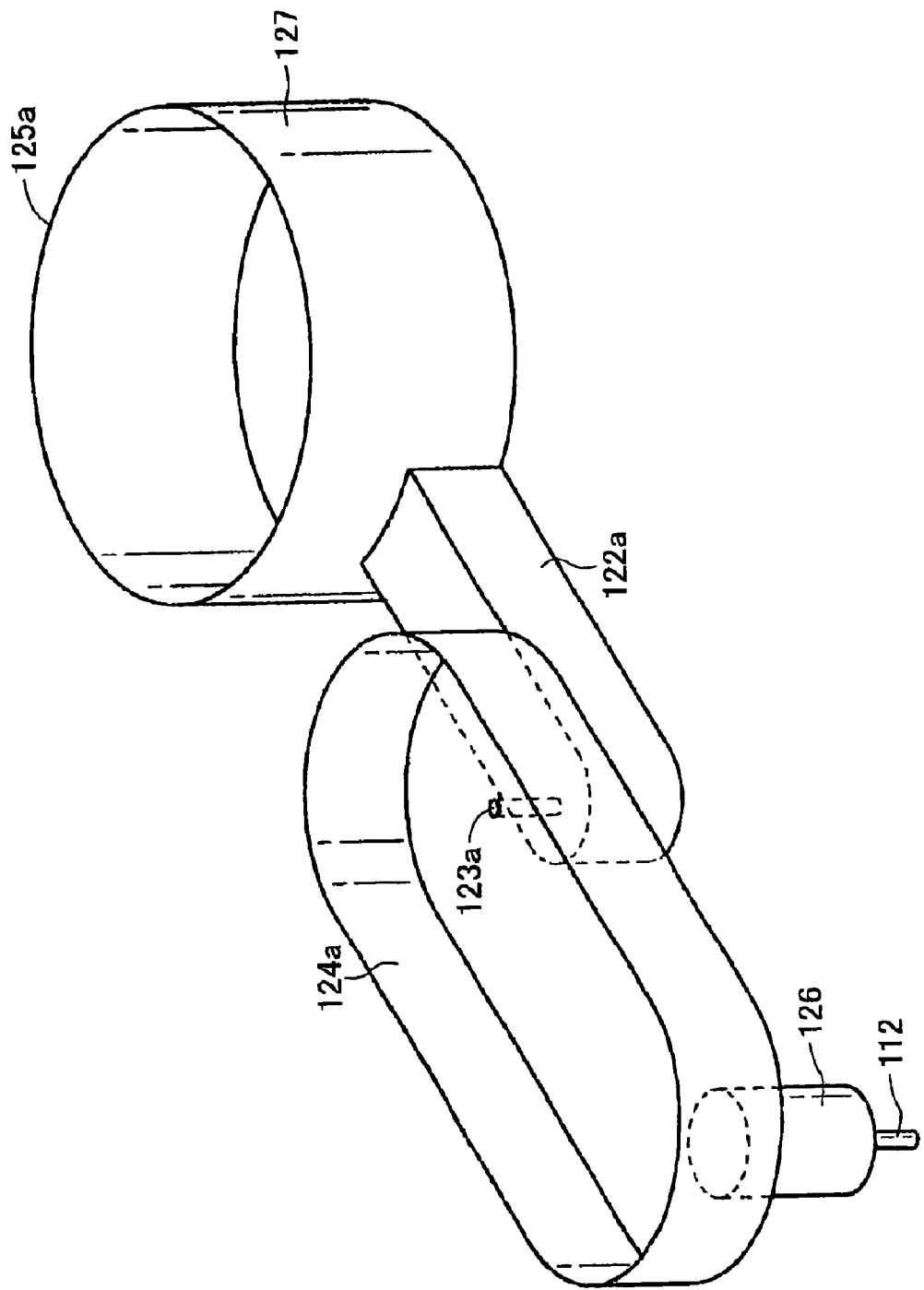
FIG. 4 is an enlarged and see-through perspective view illustrating the construction of a sample solution flow channel in the micropipette shown in FIG. 3.
Figure 5:
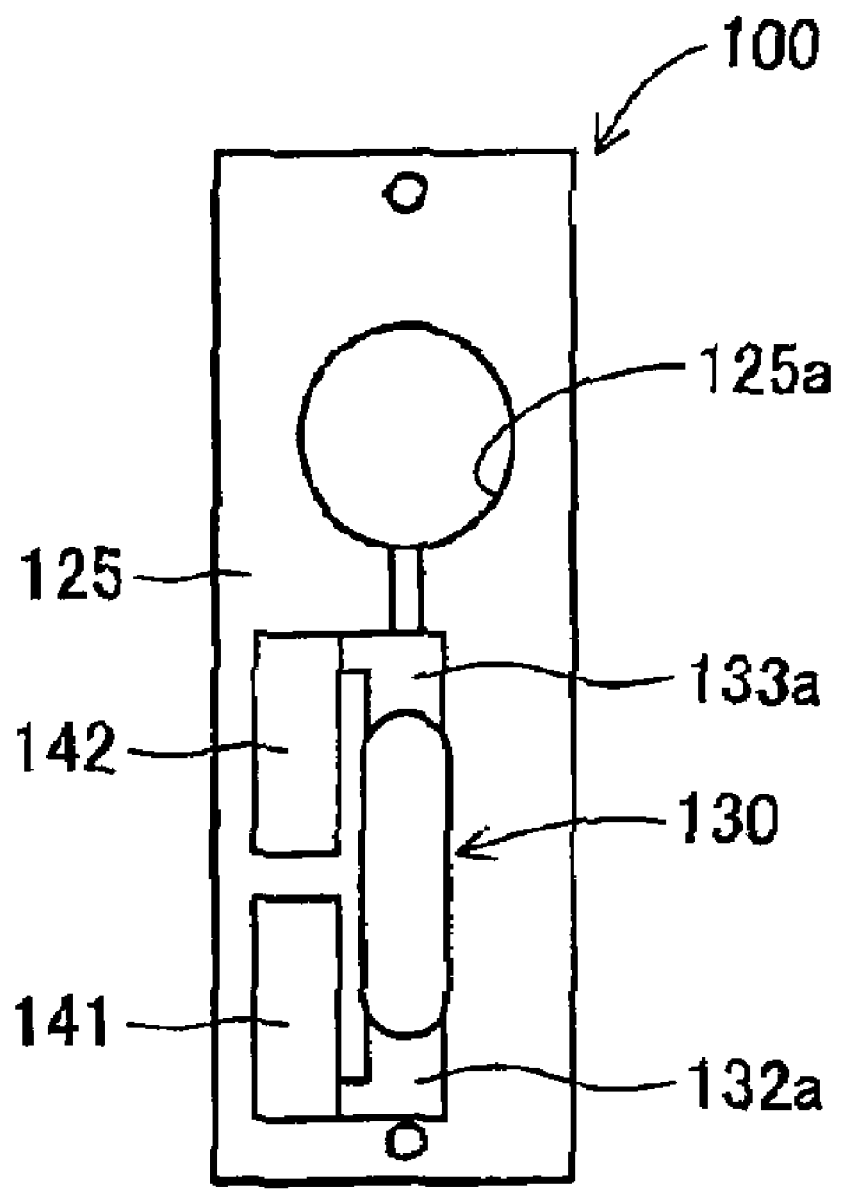
FIG. 5 is an enlarged plan view of the micropipette shown in FIG. 3.

Hereinafter, the structure of a micropipette (a micro object ejection part) 100, which is used to manufacture the above-described DNA chip 10, will be described in detail. FIG. 3 is an enlarged sectional view of the micropipette 100, FIG. 4 is a see-through perspective view illustrating the construction of a flow channel for a sample solution in the micropipette 100, and FIG. 5 is a plan view of the micropipette 100.

Referring to FIG. 3, the micropipette 100 includes a nozzle plate 110, a cavity unit 120 fixed to the upper surface of the nozzle plate 110, and an actuator unit 130 fixed to the upper surface of the cavity unit 120. In the nozzle plate 110 is formed a through-hole, i.e., a nozzle 112, through which the sample solution passes.

The nozzle plate 110 is formed from a thin ceramic plate. The material of the nozzle plate 110 includes, for example, zirconium oxide, aluminum oxide, magnesium oxide, aluminum nitride, and silicon nitride. Most preferably, a material mainly containing fully stabilized zirconium oxide or a material mainly containing partially stabilized zirconium oxide is used in terms of mechanical strength and a reaction to the material of a piezoelectric/electrostrictive film or an electrode film.

The cavity unit 120 includes a connection plate 121, a flow channel plate 122, an orifice plate 123, a cavity plate 124, and an injection port plate 125. The connection plate 121, the flow channel plate 122, the orifice plate 123, the cavity plate 124, and the injection port plate 125 are formed from a thin ceramic plate. The connection plate 121, the flow channel plate 122, the orifice plate 123, the cavity plate 124, the injection port plate 125, and the nozzle plate 110 are sintered while they are stacked in order on the nozzle plate 110. As a result, they are integrally formed at the nozzle plate 110.

The connection plate 121 is disposed at the connection between the cavity plate 120 and the nozzle plate 110 such that the connection plate 121 is joined to the upper surface of the nozzle plate 110. In the connection plate 121 is formed a through-hole having the same diameter as the nozzle 112, i.e., a nozzle communication hole 121a. The nozzle communication hole 121a is connected to a cavity 124a formed in the cavity plate 124 via a sample outlet hole 126. The sample outlet hole 126 is a through-hole having a diameter greater than that of the nozzle communication hole 121a. The sample outlet hole 126 is formed through the flow channel plate 122 and the orifice plate 123.

In the flow channel plate 122 is formed a sample supply channel 122a, through which the sample solution is supplied to the cavity 124a. The sample supply channel 122a and the cavity 124a are connected with each other via an orifice 123a, which is a through-hole, having a small diameter, formed in the orifice plate 123.

The injection port plate 125 is disposed at the uppermost layer of the cavity unit 120. In the injection port plate 125 is formed a sample injection port 125a, which is a through-hole for allowing the sample solution to be injected toward the sample supply channel 122a formed in the flow channel plate 122. The sample injection port 125a and the sample supply channel 122a formed in the flow channel plate 122 are connected with each other via a sample introduction hole 127, which is a through-hole. The sample introduction hole 127 is formed through the orifice plate 123 and the cavity plate 124.

As shown in FIG. 4, a sample solution flow channel is formed in the cavity unit 120 with the above-stated construction such that the sample solution flow channel extends from the sample injection port 125a to the nozzle 112. Specifically, the dimension of the orifice 123a is set such that, when the cavity 124a is pressurized, the sample solution in the cavity 124a does not flow backward to the sample supply channel 122a through the small-diameter orifice 123a but flows out toward the nozzle 112 through the sample outlet hole 126, and therefore, micro drops of the sample solution are ejected to the outside from the nozzle 112.

Referring back to FIG. 3, the actuator unit 130 includes a piezoelectric/electrostrictive layer 131, a lower electrode 132 fixed to the lower surface of the piezoelectric/electrostrictive layer 131, and an upper electrode 133 fixed to the upper surface of the piezoelectric/electrostrictive layer 131. The piezoelectric/electrostrictive layer 131 is disposed at a predetermined position corresponding to the cavity 124a (i.e., right above the cavity 124a). The lower electrode 132 is fixed to the upper surface of the injection port plate 125, and therefore, the actuator unit 130 is fixed to the upper surface of the cavity unit 120. The actuator unit 130 is constructed such that the actuator unit 130 changes the interior volume of the cavity 124a, when drive voltage is applied between the lower electrode 132 and the upper electrode 133, to eject a predetermined amount of the sample solution from the nozzle 112.

The lower electrode 132 is connected to a lower electrode wiring pattern 132a, which is a conductive film formed at the upper surface of the injection port plate 125. The upper electrode 133 is connected to an upper electrode wiring pattern 133a, which is a conductive film formed at the upper surface of the injection port plate 125.

As shown in FIG. 5, a lower electrode input terminal 141 is formed at the upper surface of the injection port plate 125. The lower electrode input terminal 141 is connected to the lower electrode wiring pattern 132a. Also, an upper electrode input terminal 142 is formed at the upper surface of the injection port plate 125. The upper electrode input terminal 142 is connected to the upper electrode wiring pattern 133a. The lower electrode input terminal 141 and the upper electrode input terminal 142 are connected to an external instrument that drives the actuator unit 130. Consequently, the actuator unit 130 is driven by drive voltage applied between the lower electrode input terminal 141 and the upper electrode input terminal 142 via the external instrument.

<Construction of Dispensing Apparatus>

Figure 6A:
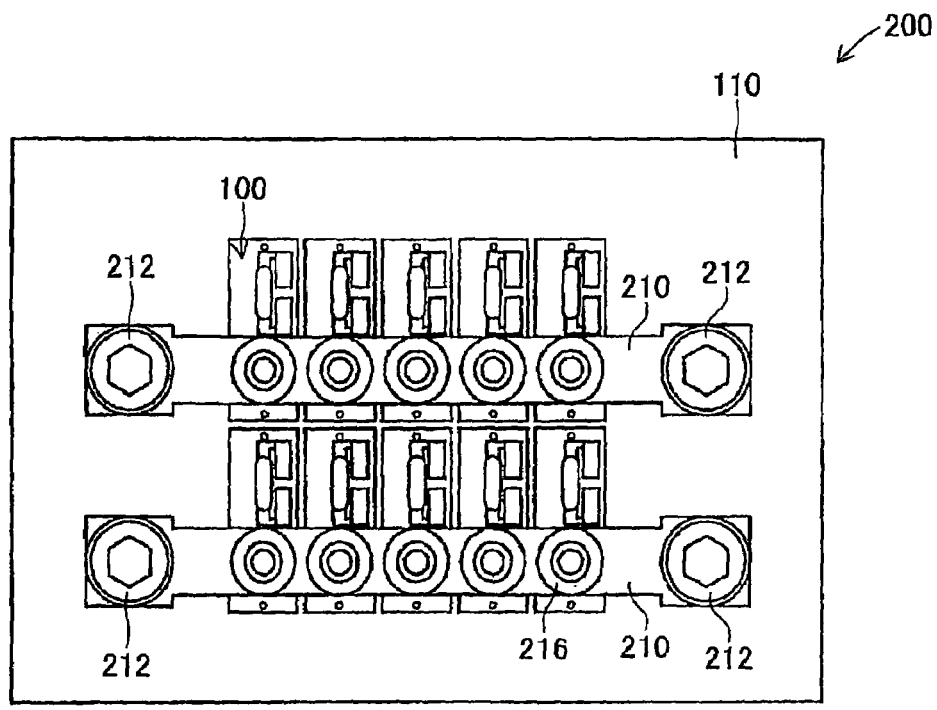
FIGS. 6A and 6B illustrate the general construction of a dispensing apparatus having the micropipette shown in FIG. 3.
Figure 6B:
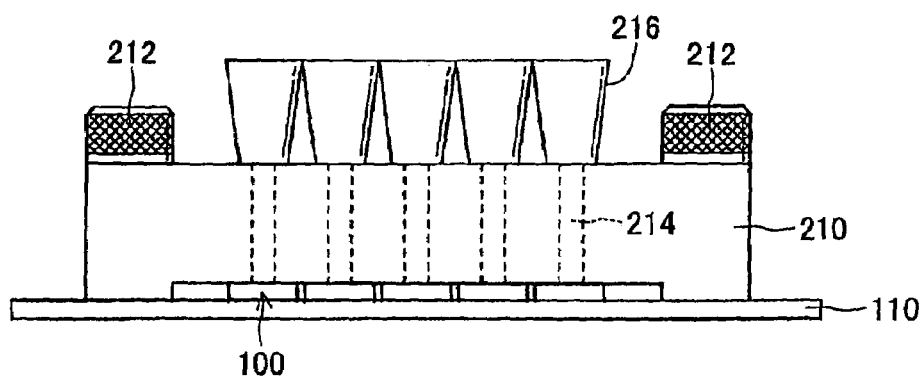
Figure 7:
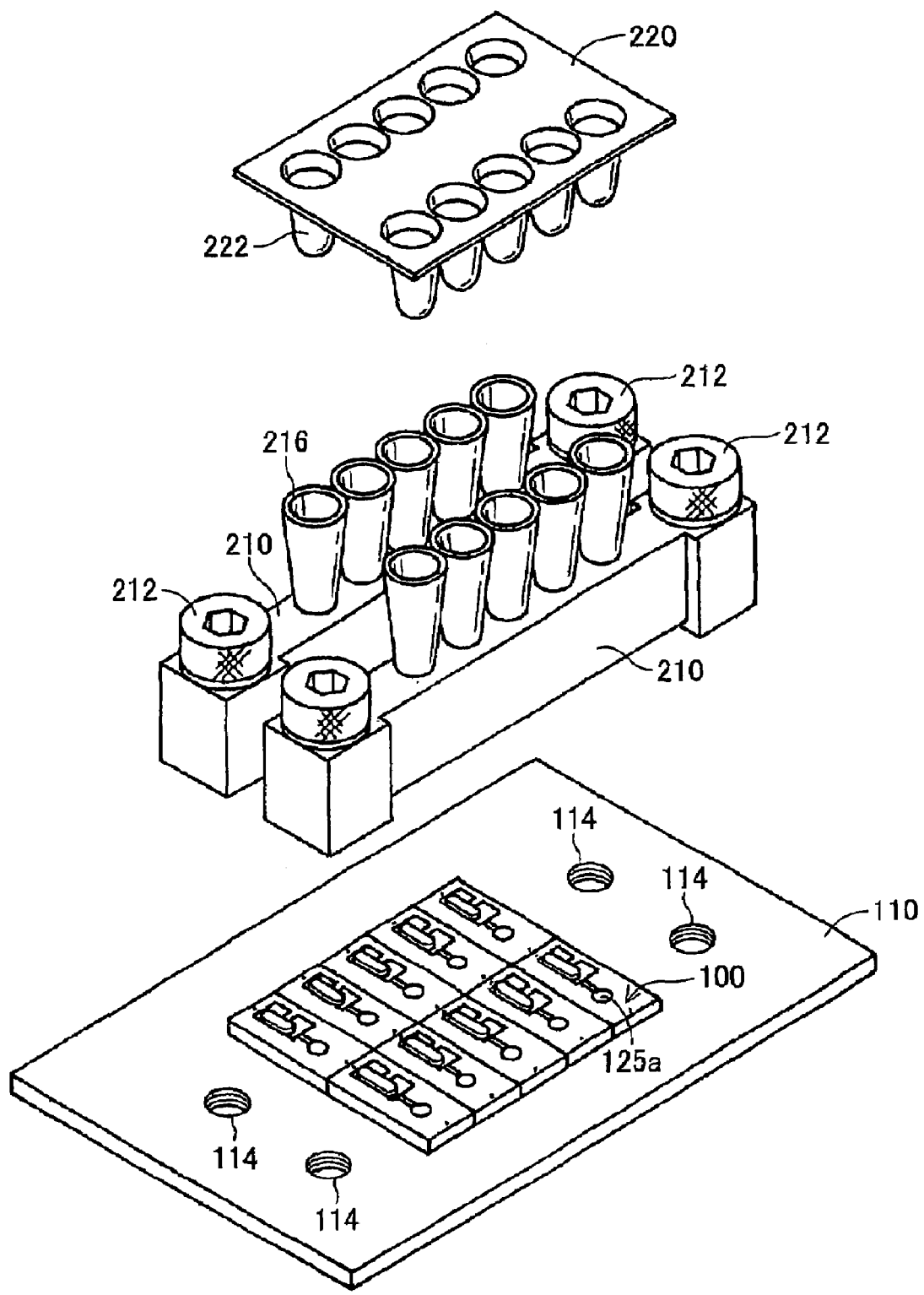
FIG. 7 is an exploded perspective view of the dispensing apparatus shown in FIG. 6.

Next, a dispensing apparatus 200 having the micropipette 100 with the above-stated construction will be described in detail. FIGS. 6A and 6B illustrate the construction of the dispensing apparatus 200. Specifically, FIG. 6A is a plan view of the dispensing apparatus 200, and FIG. 6B is a side view of the dispensing apparatus 200. FIG. 7 is an exploded perspective view of the dispensing apparatus 200.

As shown in FIG. 6A, the dispensing apparatus 200 includes a plurality (10 in the drawing) of micropipettes 100 arranged in two dimensions. All the micropipettes 100 have a common nozzle plate 110, the construction of which has already been described above. The common nozzle plate 110 is a ceramic plate.

The dispensing apparatus 200 includes sample introduction members 210 for introducing the sample solution to the respective sample injection ports 125a of the micropipettes 110 (see FIG. 5). As shown in FIGS. 6A and 6B, the sample introduction members 210 are connected to the upper surfaces of the micropipettes 110 arranged in the two dimensions. As shown in FIG. 7, the sample introduction members 210 are fixed to the upper surface of the nozzle plate 110 by means of threaded holes 114 formed in the nozzle plate 110 and fixing bolts 212.

Referring to FIG. 6B, sample injection channels 214, which are constructed in the shape of a through-hole, are formed in each sample introduction member 210. The openings at the lower ends of the sample injection channels 214 are connected to the corresponding sample injection ports 125a of the micropipettes 110 (see FIG. 5). Also, the openings at the upper ends of the sample injection channels 214 are connected to the lower ends of introduction tubes 216, which are constructed in the shape of a trumpet whose diameter gradually increases upward.

Referring to FIG. 7, the plural introduction tubes 216 arranged in two dimensions are disposed and constructed such that the introduction tubes 216 are coupled with plural sample storage portions 222, which are formed at a cartridge 220 that stores a sample solution, while the sample storage portions 222 protrude downward from the cartridge 220. The cartridge 220 is formed by injection molding of a soft synthetic resin. The cartridge 220 is constructed such that openings are formed at the bottoms of the sample storage portions 222 using a needle, and therefore, the sample solution stored in the sample storage portions 222 is introduced into the introduction tubes 216, whereby different kinds of sample solutions are supplied to the respective sample injection ports 125a.

<General Construction of Flight State Detection Apparatus According to a Preferred Embodiment>

Figure 8:
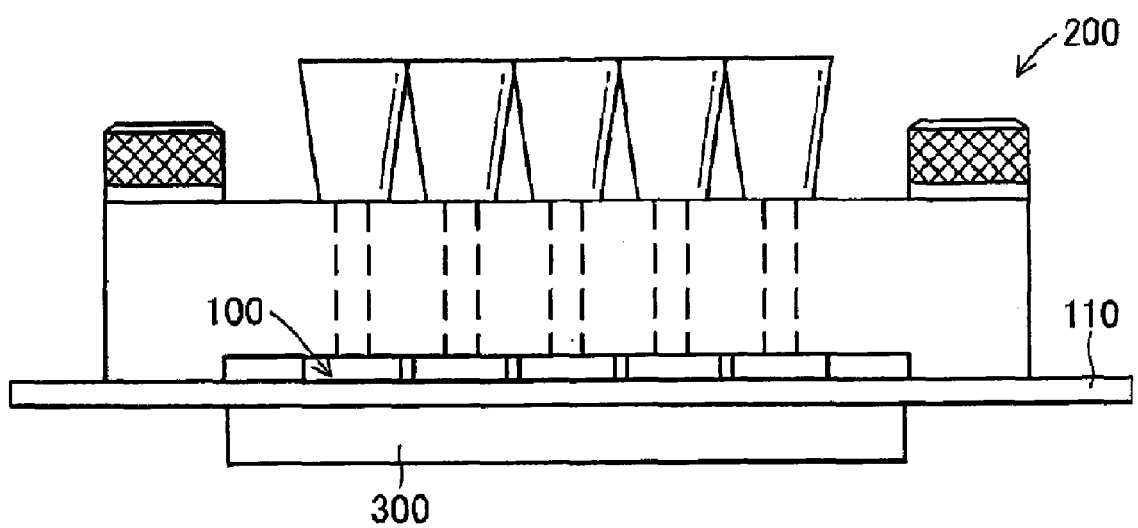
FIG. 8 is a side view illustrating a flight state detection apparatus according to a preferred embodiment of the present invention, which is mounted in the dispensing apparatus shown in FIG. 6.

Next, the general construction of a flight state detection apparatus according to a preferred embodiment of the present invention will be described in detail. FIG. 8 is a side view illustrating a flight state detection apparatus 300 mounted below the nozzle plate 110, having sample solution ejection ports, of the above-described dispensing apparatus 200. For example, the DNA chip substrate 12 shown in FIG. 1 and the flight state detection apparatus 300 are disposed on an X-Y stage (not shown) such that the flight state detection apparatus 300 can be located below the nozzle plate 110 in a predetermined positional relationship when the X-Y stage is driven.

Referring to FIG. 8, the flight state detection apparatus 300 is constructed such that the flight state detection apparatus 300 can detect whether or not the sample solution is accurately ejected from the respective micropipettes 100 of the dispensing apparatus 200. Hereinafter, the concrete construction of the flight state detection apparatus 300 according to the present invention will be described.

<Construction of Flight State Detection Apparatus According to First Embodiment>

Figure 9A:
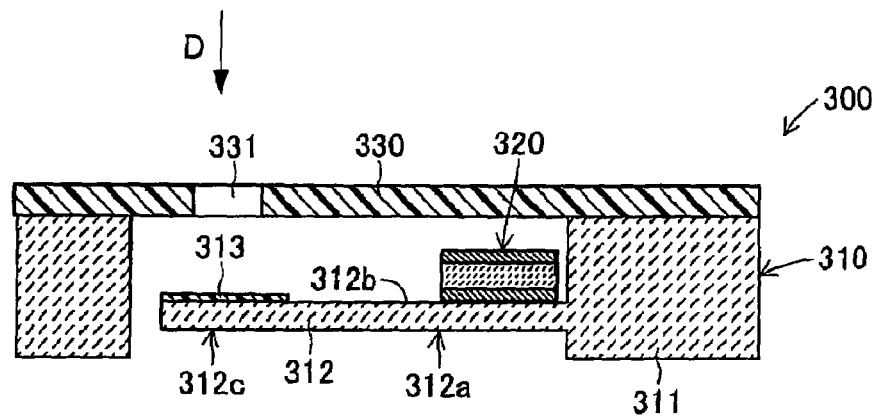
FIGS. 9A to 9C illustrate the construction of a first embodiment of the flight state detection apparatus shown in FIG. 8.

FIG. 9A is an enlarged side sectional view of the flight state detection apparatus 300 according to the first embodiment.

As shown in FIG. 9A, the flight state detection apparatus 300 includes a sensor substrate 310, a piezoelectric/electrostrictive element 320, and an aperture plate 330.

The sensor substrate 310 is constructed from a plate-shaped member. Preferably, the sensor substrate 310 is made of ceramic. For example, fully stabilized or partially stabilized zirconia, alumina, magnesia, or silicon nitride may be used as the ceramic for the sensor substrate 310. Most preferably, the fully stabilized or partially stabilized zirconia can be used since the fully stabilized or partially stabilized zirconia has high tenacity and high mechanical strength, and furthermore, the fully stabilized or partially stabilized zirconia has small reaction to a piezoelectric/electrostrictive film forming the piezoelectric/electrostrictive element or the material of the electrode, although the fully stabilized or partially stabilized zirconia is constructed in the shape of a thin plate.

The sensor substrate 310 includes a thick support part 311 and a vibrating plate (vibration generating part) 312. The thick support part 311 and the vibrating plate 312 are integrally formed to constitute a single body. The thick support part 311 has a thickness greater than the vibrating plate 312, which is formed from a plate-shaped member. The vibrating plate 312 is a plate-shaped member extending along the longitudinal direction (along the right-and-left direction in the drawing). The vibrating plate 312 is supported by the thick support part 311 in a cantilever shape.

The piezoelectric/electrostrictive element 320 is attached to a detection part 312a, which is the fixed end of the vibrating plate 312. In this embodiment, the piezoelectric/electrostrictive element 320 is fixedly attached to the inside surface 312b, which is the upper surface in the drawing, of the vibrating plate 312. The piezoelectric/electrostrictive element 320 is constructed such that the piezoelectric/electrostrictive element 320 can convert vibration generated at the cantilever-type vibrating plate 312 into an electric signal. Furthermore, the thickness of the piezoelectric/electrostrictive element 320 is relatively small as compared to the vibrating plate 312 (For convenience of the description, the thickness of the piezoelectric/electrostrictive element 320 is exaggeratedly shown in FIG. 9A. The same conditions will be applied to the following drawings, i.e., FIGS. 10 to 22).

A coating layer 313 is formed on the inside surface 312b of a target part 312c, which is the free end of the vibrating plate 312 (one end of the vibrating plate in the longitudinal direction). The coating layer 313 is constructed from a thin film made of a material having a low affinity (wettability) for micro drops of the sample solution. For example, since the sample solution used to form the above-described DNA chip 10 (see FIGS. 1 and 2) is an aqueous solution, a water-repellent material (a fluorine-based synthetic resin) is used for the coating layer 313.

The aperture plate 330 is disposed on the sensor substrate 310 such that the aperture plate 330 is opposite to the inside surface 312b of the vibrating plate 312. In the aperture plate 330, an aperture 331 is formed which is a through-hole for allowing the micro drops to pass therethrough. The aperture plate 330 is disposed such that the aperture 331 is opposite to the nozzle 112 (see FIG. 3) formed at the nozzle plate 110 (see FIG. 8) of the micropipette 100.

Figure 9B:
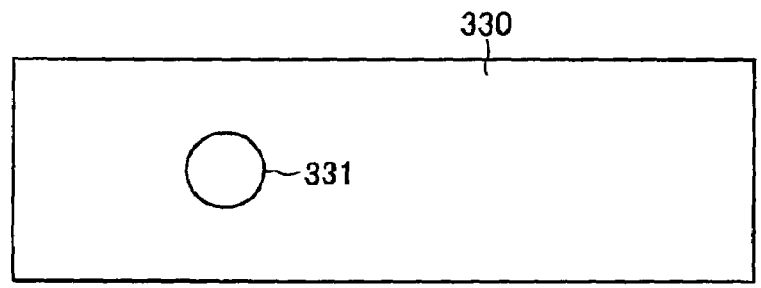
Figure 9C:
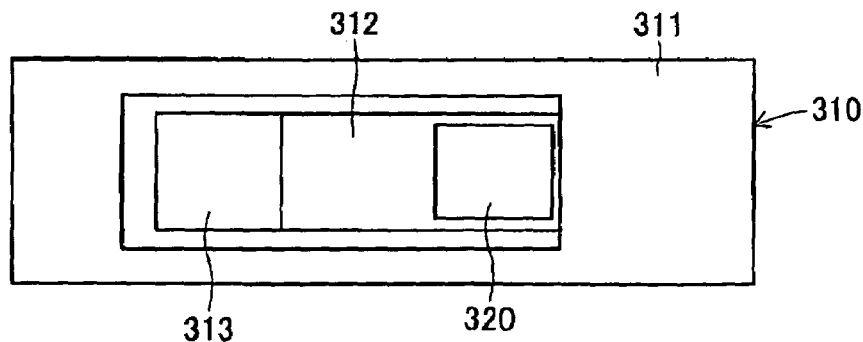

FIG. 9B is a plan view of the flight state detection apparatus 300 (a view illustrating the flight state detection apparatus 300 shown in FIG. 8 when seen from the nozzle plate 110 side of the micropipette 100). FIG. 9C is a plan view of the flight state detection apparatus 300 with the aperture plate 330 being removed. As shown in FIGS. 9A to 9C, the aperture 331 is located such that the aperture 331 is opposite to the coating layer 313 formed at the target part 312c. Also, as shown in FIG. 9A, the aperture 331 is located at a higher position than the coating layer 313 formed at the target part 312c, i.e., at the upper stream side in the flight direction D of the micro drops.

As described above, the flight state detection apparatus 300 is constructed such that the micro drops which are flying along a predetermined flight route in the flight direction D can pass through the aperture 331 to collide with the target part 312c (the coating layer 313), and vibration generated in the vibrating plate 312 due to the collision can be converted into an electric signal by the piezoelectric/electrostrictive element 320.

<<Construction of Piezoelectric/Electrostrictive Element>>

Figure 10A:
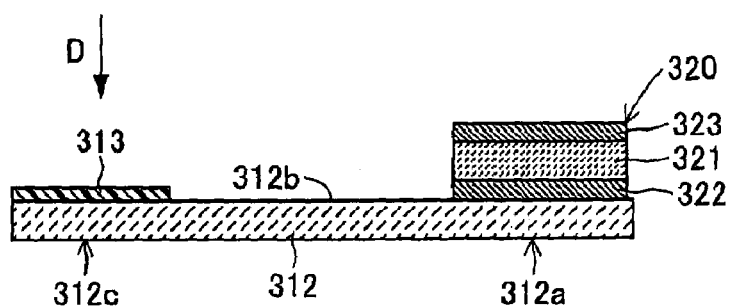
FIGS. 10A to 10C illustrate principal components of the flight state detection apparatus shown in FIG. 9.

FIG. 10A is an enlarged sectional view of the vibrating plate 312 and its surroundings. As shown in FIG. 10A, the piezoelectric/electrostrictive element 320 includes a piezoelectric/electrostrictive layer 321, a lower electrode 322 formed at one-side surface of the piezoelectric/electrostrictive layer 321, and an upper electrode 323 formed at the other-side surface of the piezoelectric/electrostrictive layer 321. The piezoelectric/electrostrictive layer 321 is constructed from a thin plate having a piezoelectric effect and a converse piezoelectric effect, for example, a thin plate made of a piezoelectric/electrostrictive material (PZT or the like). The lower electrode 322 and the upper electrode 323 are constructed from a metal film.

<<Construction of Vibrating Plate>>

Figure 10B:
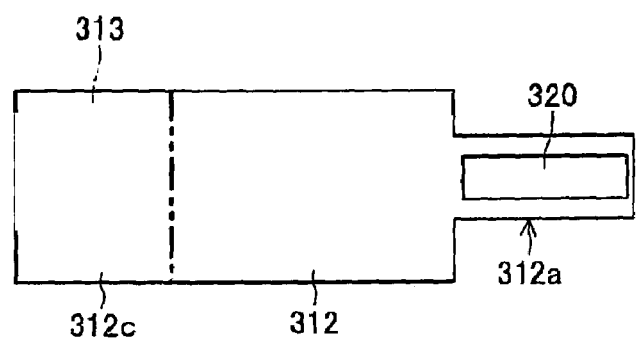

FIG. 10B is an enlarged plan view of the vibrating plate 312 and its surroundings.

As shown in FIG. 10B, the detection part 312a of the vibrating plate 312 has a smaller width than that of the other part of the vibrating plate 312. Specifically, the plane shape of the vibrating plate 312 is set such that, when the micro drops of the sample solution fly from above (from above in the FIG. 10A) to collide with the target part 312c (the coating layer 313), and therefore, vibration is generated in the vibrating plate 312, stress is concentrated on the detection part 312a, and large voltage is generated in the piezoelectric/electrostrictive element 320 due to the stress concentration.

Figure 10C:
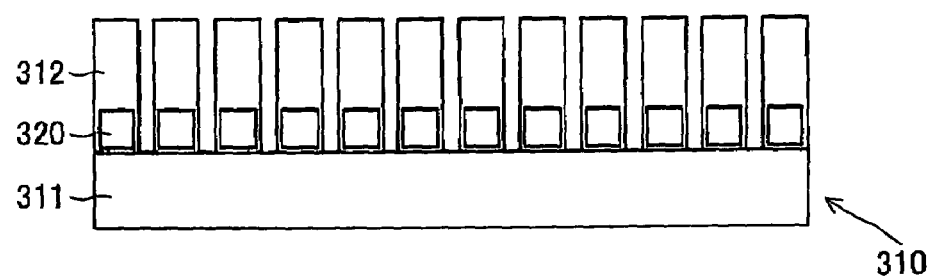

FIG. 10C is a plan view of the sensor substrate 310. As shown in FIG. 10C, plural vibrating plates 312 are formed at the sensor substrate 310 such that the vibrating plates 312 extend from the thick support part 311 approximately in the horizontal direction.

<Circuit Construction for Flight State Detection>

Subsequently, the construction of a control circuit 340 for determining the ejection state of the micro drops of the sample solution from the micropipette 100 (see FIG. 8) using the above-described construction of the apparatus will be described with reference to FIG. 11.

The control circuit 340 includes a voltage acquisition part 341 for acquiring the voltage generated in the piezoelectric/electrostrictive element 320, a drive part 342 for applying a drive voltage to the piezoelectric/electrostrictive element 320, an operation and control part 343 connected to the voltage acquisition part 341 and the drive part 342, and a drive part 344 for applying a drive voltage to the respective micropipettes 100.

The voltage acquisition part 341 is electrically connected to the piezoelectric/electrostrictive element 320 for acquiring an electromotive force generated in the piezoelectric/electrostrictive element 320 when the micro drops of the sample solution collide with the target part 312c (see FIG. 10A). The drive part 342 is electrically connected to the piezoelectric/electrostrictive element 320 for applying a drive voltage to the piezoelectric/electrostrictive element 320, such that the piezoelectric/electrostrictive element 320 can be driven, to forcibly vibrate the vibrating plate 312 (see FIGS. 10A to 10C).

The drive part 342 is constructed such that a voltage having an arbitrary waveform (including a direct current, and also including various waveforms, such as a sine waveform, a rectangular waveform, a pulse waveform, etc., in an alternating current) can be applied to the piezoelectric/electrostrictive element 320 under the control of the operation and control part 343.

The operation and control part 343 is constructed such that the operation and control part 343 receives a signal from the voltage acquisition part 341 and properly operates the received signal to detect the vibration state (including the magnitude of the vibration, the vibration mode, and the resonant frequency) of the vibrating plate 312 (see FIGS. 10A to 10C). Also, the operation and control part 343 is constructed such that the operation and control part 343 applies a drive signal to the drive part 342 to control the driving of the piezoelectric/electrostrictive element 320. Furthermore, the operation and control part 343 is connected to the respective micropipettes 100 via the drive part 344 for controlling the ejection of the sample solution from the respective micropipettes 100.

<Description of Operation of Flight State Detection Apparatus According to First Embodiment>

Next, the operation of the flight state detection apparatus 300 with the above-stated construction according to the first embodiment will be described in detail with reference to the accompanying drawings.

<<Manufacturing Process of DNA Chip>>

First, the manufacturing process of the DNA chip 10 shown in FIG. 1 will be described. The manufacturing process includes a pre-treatment process of forming a sample support layer 14 (see FIG. 2), which is a poly-L-lysine layer, on the surface of the DNA chip substrate 12, a sample manufacturing process of manufacturing a sample solution containing DNA pieces, and a supply process of supplying the manufactured sample solution onto the DNA chip substrate 12.

The pre-treatment process is carried out as follows. First, the DNA chip substrate 12 is soaked in a predetermined alkali solution at the room temperature for at least two hours. As the alkali solution, for example, there may be used a solution obtained by dissolving NaOH in distilled water, adding ethanol in the mixture, and stirring the mixture until the mixture becomes fully transparent. After that, the DNA chip substrate 12 is taken out of the alkali solution, and is then washed in distilled water. Subsequently, the DNA chip substrate 12 is soaked in a poly-L-lysine solution manufactured by adding poly-L-lysine in distilled water for approximately one hour. After that, the DNA chip substrate 12 is taken out of the poly-L-lysine solution, and the poly-L-lysine solution remaining on the DNA chip substrate 12 is removed by centrifugal separation. Subsequently, the DNA chip substrate 12 is dried at 40° C. for approximately 5 minutes. In this way, a DNA chip substrate 12 having the poly-L-lysine sample support layer 14 formed on the surface thereof is obtained.

The sample manufacturing process includes an amplifying process of amplifying the base sequence of the DNA pieces, using polymerase chain reaction (PCR), to obtain a PCR product, a powder producing process of drying the obtained PCR product to obtain DNA powder, and a mixing process of dissolving the obtained DNA powder in a buffer solution. In the powder producing process, first, sodium acetate of 3M (=3 mol/l) and isopropanol are added to the PCR product, and the mixture is left for a few hours. After that, the solution is centrifugally separated, and therefore, the DNA pieces are precipitated. The precipitated DNA pieces are rinsed using ethanol, are centrifugally separated, and are then dried. As a result, DNA powder is produced. In the mixing process, a Tris-EDTA (TE) buffer solution is added to the DNA powder, and the mixture is left for a few hours until the DNA powder is fully dissolved in the buffer solution. As a result, a sample solution is prepared. The concentration of the sample solution prepared at this step is 1 to 10 μg/μl The sample solution obtained as described above is stored in the sample storage portions 222 of the cartridge 220 shown in FIG. 7. Since the cartridge 220 is mounted to the dispensing apparatus 200 shown in FIG. B, the sample solution is supplied into the respective micropipettes 100 in the dispensing apparatus 200. And the micro drops of the sample solution are ejected toward the DNA chip substrate 12 (see FIG. 1) from the respective micropipettes 100, and therefore, the micro drops of the sample solution are supplied onto the DNA chip substrate 12. As a result, plural micro spots S of the sample solution are formed on the DNA chip substrate 12 in a predetermined array. In this way, the DNA chip 10 is manufactured.

Here, it is difficult to observe the micro drops of the sample solution with the naked eye. For this reason, the determination as to whether or not the micro drops of the sample solution are properly formed on the DNA chip substrate 12 in the predetermined array (whether the ejecting operation is not correctly carried out, for example, the micro drops are not ejected, in one or more specific micropipettes 110) cannot be performed with the naked eye. On the other hand, it is possible to determine whether the micro drops are not ejected by scanning the ejection route of the micro drops with a laser beam. However, the construction of an apparatus for determining whether the ejecting operation is not correctly carried out in the respective micropipettes 100 by scanning the laser beam as described above is very expensive.

On the contrary, the determination as to whether the ejecting operation is not correctly carried out in the respective micropipettes 100 of the dispensing apparatus 200 is accomplished using the flight state detection apparatus 300 according to the preferred embodiment of the present invention as shown in FIG. 8. As described above, the construction of the flight state detection apparatus 300 is very simple, and therefore, the manufacturing costs of the flight state detection apparatus 300 are very low. Although the construction of the flight state detection apparatus 300 is very simple as described above, it is possible for the flight state detection apparatus 300 to accurately perform the determination as to whether the ejecting operation is not correctly carried out.

<<Description of Flight State Detecting Operation According First Embodiment>>

Next, the determining operation of the ejection state of the micro drops of the sample solution in the micropipettes 100 using the flight state detection apparatus 300 according to this embodiment (including the above-described respective embodiments) will be described in detail with reference to FIGS. 8 to 12. Here, FIGS. 12A and 12B illustrate the vibration state of the vibrating plate 312 (see FIGS. 9A to 9C and 10A to 10C).

As shown in FIG. 8, the flight state detection apparatus 300 is disposed below the nozzle plate 110 of the micropipettes 100. The driving operation of the dispensing apparatus 200 is controlled by the operation and control part 343 and drive part 344 as shown in FIG. 11. Specifically, under the control of the operation and control part 343, a drive voltage from the drive part 344 is applied to the actuator units 130 (see FIG. 5) of the respective micropipettes 100 mounted in the dispensing apparatus 200, whereby the respective micropipettes 100 are driven. As a result, micro drops of the sample solution are ejected to the flight state detection apparatus 300 from the respective micropipettes 100.

Referring to FIGS. 9A to 9C, after the micro drops of the sample solution are ejected as described above, the micro drops pass through the aperture 331, and then collide with the target part 312c (the coating layer 313) of the vibrating plate 312 in regular sequence. The vibrating plate 312 is vibrated by this collision. As a result, an electromotive force is generated in the piezoelectric/electrostrictive element 320. That is to say, voltage is generated between the lower electrode 322 and the upper electrode 323 shown in FIGS. 10A to 10C depending upon the vibration state of the vibrating plate 312.

Figure 12A:
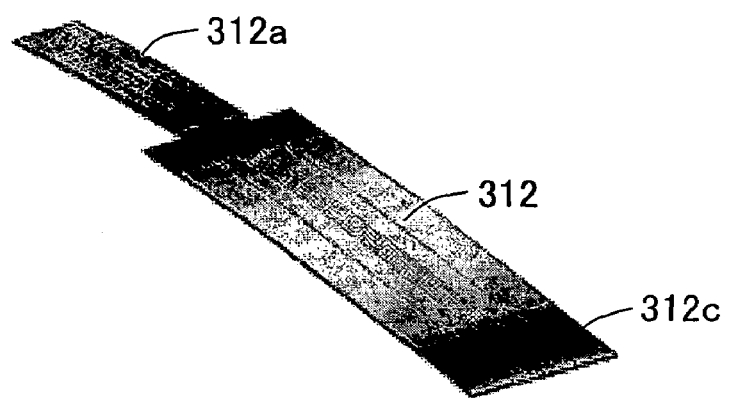
FIGS. 12A and 12B illustrate the vibration state of a vibrating plate shown in FIGS. 9 and 10.

For example, in the case that the micro drops collide with the middle of the target part 312c in the lateral direction of the target part 312c (in the case that the flight direction of the micro drops coincides with the predetermined direction D), as shown in FIG. 12A, the vibrating plate 312 is vibrated such that the vibrating plate 312 is bent (a primary bending mode). As a result, stress is generated in the detection part 312a. The generated stress is converted into an electromotive force by the piezoelectric/electrostrictive element 320 (see FIGS. 10A to 10C).

On the other hand, in the case that the micro drops collide with a position offset from the middle of the target part 312c in the lateral direction of the target part 312c (in the case that the flight direction of the micro drops does not coincide with the predetermined direction D), as shown in FIG. 12B, the vibrating plate 312 is vibrated such that the vibrating plate 312 is twisted (a twisting mode). As a result, stress, which is smaller than the stress generated in the bending mode as shown in FIG. 12A, is generated in the detection part 312a. Consequently, an electromotive force, which is smaller than the electromotive force generated in the bending mode, is generated in the piezoelectric/electrostrictive element 320 (see FIGS. 10A to 10C).

In the case that the flight route of the micro drops is further deviated from the predetermined flight route, the micro drops do not pass through the aperture 331 but collide with the upper surface of the aperture plate 330. In this case, the micro drops do not collide with the target part 312c, and therefore, no vibration is generated in the vibrating plate 312 (or the amplitude of the vibrating plate is converged toward zero).

In this way, a voltage corresponding to the vibration state of the vibrating plate 312 (i.e., the collision state between the micro drops and the target part 312c) is generated in the piezoelectric/electrostrictive element 320.

Figure 11:
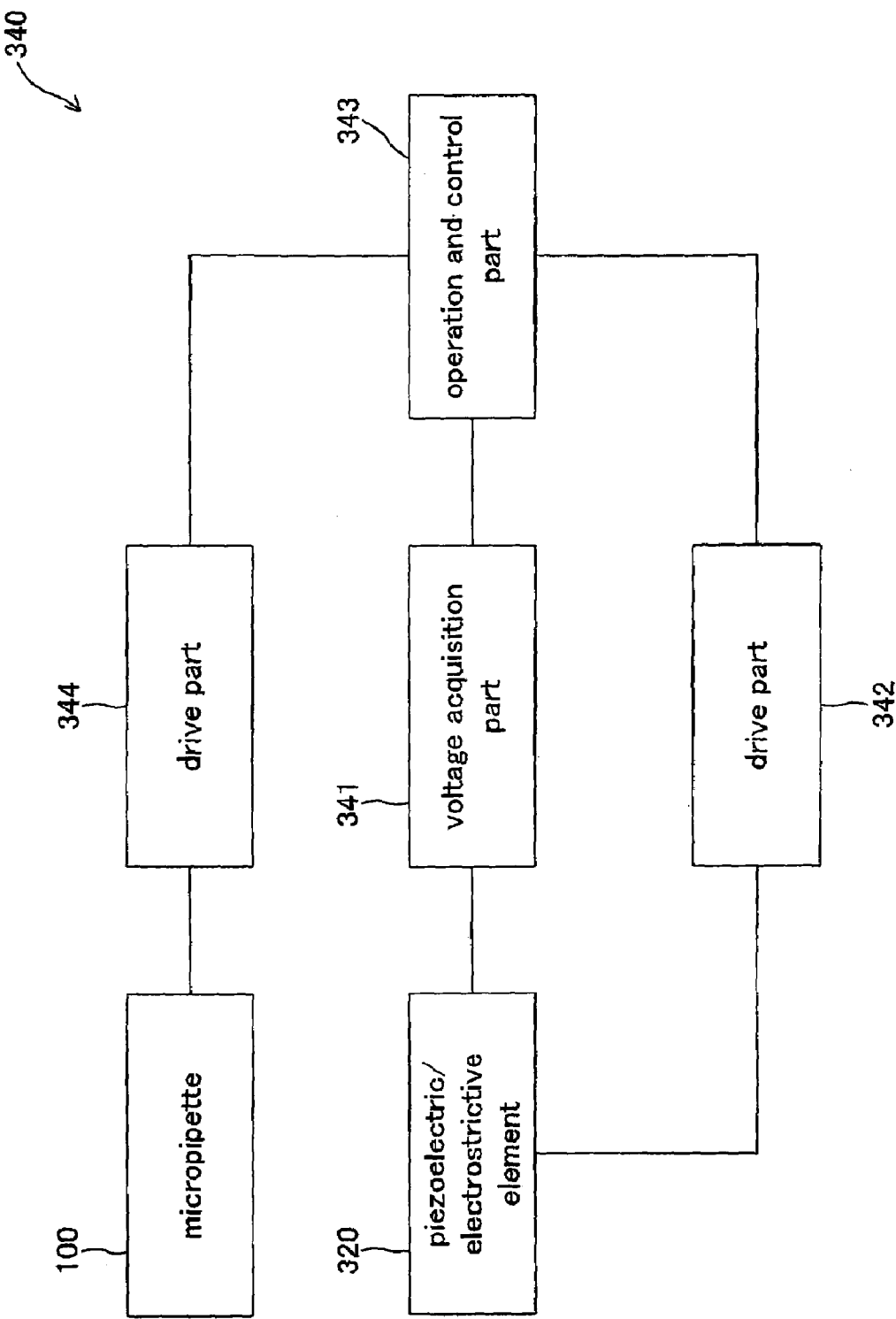
FIG. 11 is a view illustrating a circuit construction for determining the ejection state of liquid drops of a sample solution using the flight state detection apparatus shown in FIG. 9.
Figure 12B:
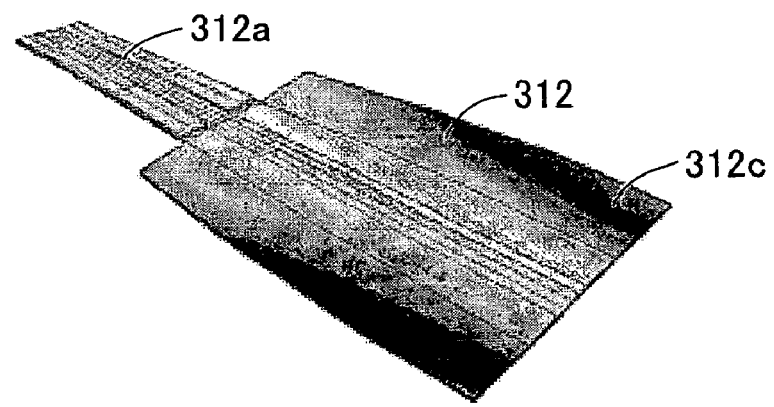

Referring to FIG. 11, the voltage generated in the piezoelectric/electrostrictive element 320 is acquired by the voltage acquisition part 341, and the electromotive force acquired by the voltage acquisition part 341 is operated by the operation and control part 343, whereby the vibration state of the vibrating plate 312 is detected.

Referring to FIGS. 10A to 10C and 11, on the assumption that the resonant frequency of the vibrating plate 312 is $f0$, the operation and control part 343 drives the micropipettes 100 at a specific frequency $f1$ satisfying the following inequality:

$(n-0.2)f1 \leq f0 \leq (n+0.25)f1$ [n is a natural number].

As a result, the micro drops of the sample solution are ejected one by one for a period T corresponding to the specific frequency $f1$.

Also, on the assumption that the time necessary for the vibrating plate 312 to absorb the kinetic energy of the micro drops is T1, and the inherent period corresponding to the resonant frequency f0 is T0, the driving operation of the micropipettes 100 is controlled such that the ejection of the micro drops is carried out in the condition satisfying the following inequality:

$$T1 \leq 0.2 \, T0.$$

As a result, the vibrating plate 312 is vibrated at a frequency approximately equal to the resonant frequency of the vibrating plate 312. And the micro drops collide with the target part 312c one by one while the micro drops are synchronized with the vibration of the vibrating plate 312. Consequently, the vibration of the vibrating plate 312 is effectively prevented from being varied due to the collision between the micro drops and the vibrating plate 312.

According to the construction of this embodiment, as shown in FIGS. 10B and 12, the detection part 312a of the vibrating plate 312 has a smaller width than that of the other part of the vibrating plate 312. Consequently, when the micro drops of the sample solution fall from above to collide with the target part 312c, and therefore, vibration is generated in the vibrating plate 312, stress is concentrated on the detection part 312a. Due to the stress concentration, large voltage is generated in the piezoelectric/electrostrictive element 320.

<<Description of Spray Disposal Operation of Sample Solution According to First Embodiment>>

Referring back to FIGS. 9A to 9C, most spray of the sample solution, which is generated when the micro drops of the sample solution collide with the coating layer 313, is not attached to the surface of the coating layer 313 for a long time but drops due to gravity. As a result, most of the sample solution is removed from the inside surface 312b of the vibrating plate 312. However, some of the spray may not be completely removed from the inside surface 312b of the vibrating plate 312. In other words, some of the spray may be left on the inside surface 312b of the vibrating plate 312.

The remaining spray may be removed from the inside surface 312b of the vibrating plate 312 by forcibly vibrating the vibration plate 312 from the outside as will be described below.

Referring to FIG. 11, while the driving operation of the micropipettes 100 is stopped (the ejection of the micro drops of the sample solution is stopped), the drive part 342 applies a drive voltage having the above-described resonant frequency f0 to the piezoelectric/electrostrictive element 320 under the control of the operation and control part 343. As a result, the piezoelectric/electrostrictive element 320 is driven, and the vibrating plate 312 (see FIGS. 9A to 9C) is forcibly vibrated. Consequently, the spray of the sample solution is removed from the vibrating plate 312.

<<Example of Acquisition Operation of Resonant Frequency According to First Embodiment>>

Even though the vibrating plate 312 is forcibly vibrated, a very small amount of the sample solution may be left and solidified on the vibrating plate 312. As a result, the resonant frequency of the vibrating plate 312 is changed. Here, it is possible to acquire the changed resonant frequency using the control circuit 340 shown in FIG. 11 as will be described below.

First, the drive part 342 applies a DC voltage to the piezoelectric/electrostrictive element 320 for a predetermined period of time (a time sufficiently longer than a period corresponding to the expected resonant frequency) under the control of the operation and control part 343, and then the application of the DC voltage is interrupted. As a result, free vibration with damping is generated in the piezoelectric/electrostrictive element 320. Due to this free vibration with damping, an AC voltage is generated in the piezoelectric/electrostrictive element 320. Consequently, a voltage waveform is generated in the piezoelectric/electrostrictive element 320. The voltage waveform is acquired by the operation and control part 343 through the voltage acquisition part 341. In this way, the operation and control part 343 can acquire the changed resonant frequency by acquiring the frequency of the voltage waveform. The acquired new resonant frequency is used for the drive part 342 to drive the piezoelectric/electrostrictive element 320.

Flight State Detection Apparatus According to Second Embodiment

Next, a second embodiment of the flight state detection apparatus according to the present invention will be described in detail with reference to FIGS. 13A and 13B. The components of the flight state detection apparatus according to the second embodiment identical in operation and function to those of the flight state detection apparatus according to the above-described first embodiment are omitted from the drawings. Alternatively, the components of the flight state detection apparatus according to the second embodiment identical in operation and function to those of the flight state detection apparatus according to the first embodiment are denoted by the same reference numerals as those of the first embodiment. Also, the description of the first embodiment will be quoted with respect to the second embodiment (The same conditions will be applied to the following other embodiments and modifications).

Figure 13A:
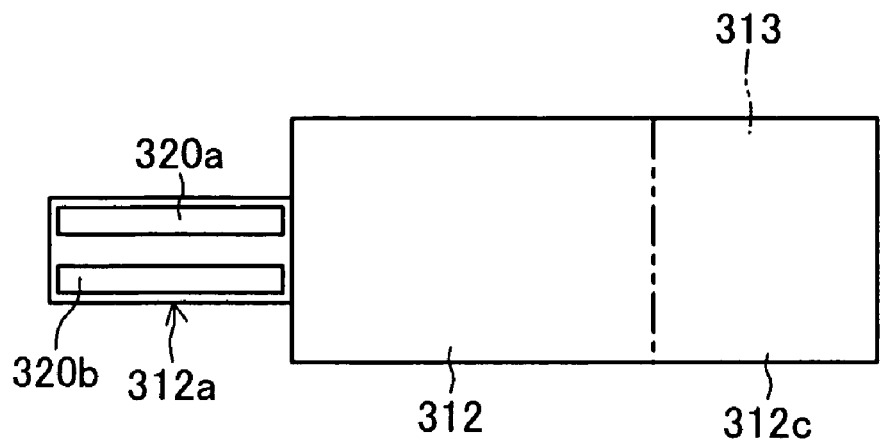
FIGS. 13A and 13B illustrate the construction of a second embodiment of the flight state detection apparatus shown in FIG. 8.
Figure 13B:
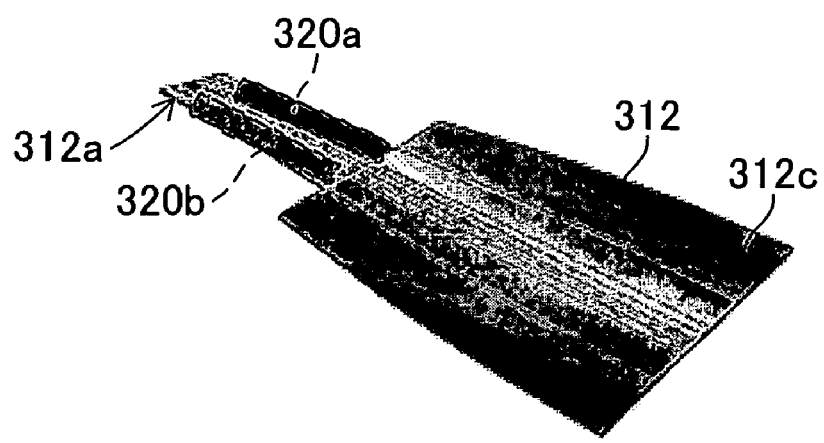

FIG. 13A is an enlarged plan view of the vibrating plate 312 according to the second embodiment and its surroundings, and FIG. 13B is an enlarged plan view illustrating the vibration state of the vibrating plate 312.

As shown in FIG. 13A, two piezoelectric/electrostrictive elements 320a and 320b are mounted at the detection part 312a of the vibrating plate 312. The piezoelectric/electrostrictive elements 320a and 320b are electrically connected to the operation and control part 343 (see FIG. 11), respectively. Also, the two piezoelectric/electrostrictive elements 320a and 320b have the same construction of the piezoelectric/electrostrictive element 320 shown in FIG. 10A. In addition, the polarizing directions of piezoelectric/electrostrictive layers of the piezoelectric/electrostrictive elements 320a and 320b (see the piezoelectric/electrostrictive layer 321 shown in FIG. 10A) are the same.

According to the above-described construction, in the case that twisting-mode vibration is generated in the vibrating plate 312, as shown in FIG. 13B, phase difference is generated by a half period between the output voltage waveform of the piezoelectric/electrostrictive element 320a and the output voltage waveform of the piezoelectric/electrostrictive element 320b. On the other hand, in the case that bending-mode vibration is generated in the vibrating plate 312, no phase difference is generated between the output voltage waveform of the piezoelectric/electrostrictive element 320a and the output voltage waveform of the piezoelectric/electrostrictive element 320b. Consequently, the vibration mode generated in the vibrating plate 312 is determined by the comparison between the output voltage waveform of the piezoelectric/electrostrictive element 320a and the output voltage waveform of the piezoelectric/electrostrictive element 320b. In this way, the collision state between the micro drops and the target part 312c of the vibrating plate 312, i.e., the flight state of the micro drops is determined.

Flight State Detection Apparatus According to Third Embodiment

Next, a third embodiment of the flight state detection apparatus according to the present invention will be described in detail with reference to FIGS. 14A to 14C.

Figure 14A:
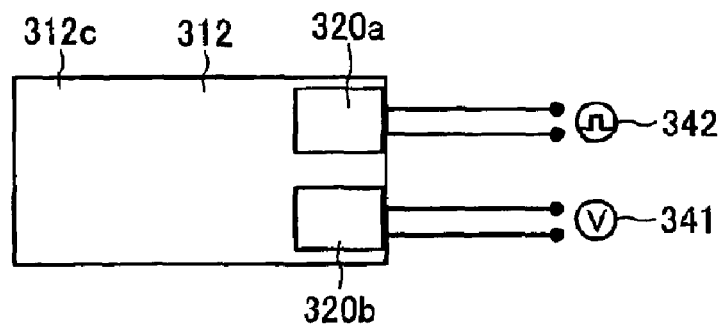
FIGS. 14A to 14C are enlarged views illustrating the construction of a third embodiment of the flight state detection apparatus shown in FIG. 8.

Referring to FIG. 14A, two piezoelectric/electrostrictive elements 320a and 320b are mounted at a single vibrating plate 312. One of the piezoelectric/electrostrictive elements, i.e., the piezoelectric/electrostrictive element 320a, is connected to the drive part 342. Also, the other piezoelectric/electrostrictive element 320b is connected to the voltage acquisition part 341. As described above, the drive part 342 is constructed such that a voltage having an arbitrary waveform (including a direct current, and also including various waveforms, such as a sine waveform, a rectangular waveform, a pulse waveform, etc., in an alternating current) can be applied to the piezoelectric/electrostrictive element 320a under the control of the operation and control part 343 (see FIG. 11) (The same conditions will be applied to the drive part 342 shown in FIGS. 14B, 14C, and 15A to 15C, which will be described below).

According to the above-described construction, in the same manner as the above-described first embodiment, a DC voltage to the piezoelectric/electrostrictive element 320a is applied by the drive part 342 for a predetermined period of time (time sufficiently longer than a period corresponding to the expected resonant frequency), and then the application of the DC voltage is interrupted. As a result, free vibration with damping is generated in a vibration system including the vibration plate 312, the piezoelectric/electrostrictive element 320a, and the piezoelectric/electrostrictive element 320b. Due to this free vibration with damping, an AC voltage is generated in the piezoelectric/electrostrictive element 320b. Consequently, a voltage waveform is generated in the piezoelectric/electrostrictive element 320b, and the resonant frequency of the vibrating plate 312 is acquired based on the voltage waveform generated in the piezoelectric/electrostrictive element 320b. The acquired new resonant frequency is used for the drive part 342 to drive the piezoelectric/electrostrictive element 320.

Also, according to the above-described construction, unlike the above-described first embodiment, the AC voltage is applied to one of the piezoelectric/electrostrictive elements, i.e., the piezoelectric/electrostrictive element 320a, from the drive part 342, and the waveform of the electromotive force generated in the other piezoelectric/electrostrictive element 320b is acquired by the voltage acquisition part 341. Consequently, it is possible to acquire the resonant frequency of the vibrating plate 312 for a short period of time. In this case, the drive part 342 outputs the AC voltage having a waveform allowing the frequency to be changed as time passes. The frequency in the case that the voltage acquired by the voltage acquisition part 341 is the maximum or in the case that the impedance or the phase is sharply changed may be chosen as the acquired value of the resonant frequency.

Furthermore, according to the above-described construction, in the same manner as the above-described second embodiment, it is possible to carry out the determination of the twisting mode based on the output of the piezoelectric/electrostrictive element 320b. In addition, even in the case that one of the piezoelectric/electrostrictive elements, i.e., the piezoelectric/electrostrictive element 320a, is also connected to the voltage acquisition part 341 (i.e., both the piezoelectric/electrostrictive elements 320a and 320b are connected to the voltage acquisition part 341), It is possible to carry out the determination of the twisting mode since this embodiment has the same construction as the above-described second embodiment.

Figure 14B:
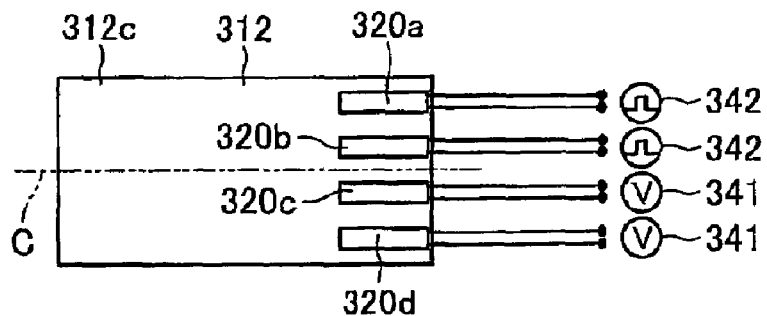

Referring to FIG. 14B, four piezoelectric/electrostrictive elements 320a to 320d are mounted at a single vibrating plate 312. The piezoelectric/electrostrictive element 320a and the piezoelectric/electrostrictive element 320d are symmetrically disposed along the lateral direction of the vibrating plate 312 about a middle line C of the vibrating plate 312 located between the piezoelectric/electrostrictive element 320a and the piezoelectric/electrostrictive element 320d. Similarly, the piezoelectric/electrostrictive element 320b and the piezoelectric/electrostrictive element 320c are symmetrically disposed along the lateral direction of the vibrating plate 312 about the middle line C of the vibrating plate 312. The piezoelectric/electrostrictive element 320a and the piezoelectric/electrostrictive element 320b are connected to the drive part 342. The piezoelectric/electrostrictive element 320c and the piezoelectric/electrostrictive element 320d are connected to the voltage acquisition part 341.

According to the above-described construction, in the same manner as the construction shown in FIG. 14A, the acquisition of the resonant frequency through the application of the DC voltage, the acquisition of the resonant frequency through the application of the AC voltage, and the determination of the twisting mode are carried out.

Figure 14C:
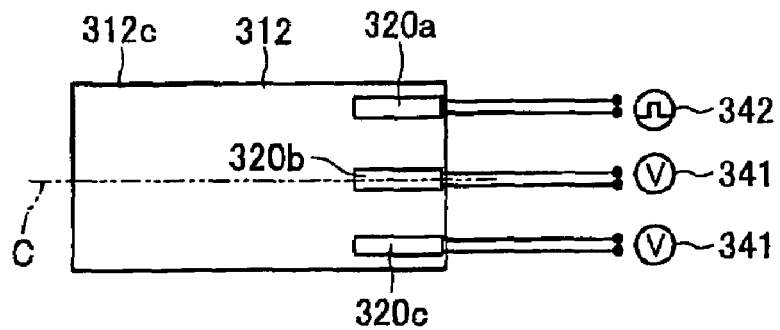

Referring to FIG. 14C, three piezoelectric/electrostrictive elements 320a to 320c are mounted at a single vibrating plate 312. The piezoelectric/electrostrictive element 320a and the piezoelectric/electrostrictive element 320c are symmetrically disposed along the lateral direction of the vibrating plate 312 about a middle line C of the vibrating plate 312 located between the piezoelectric/electrostrictive element 320a and the piezoelectric/electrostrictive element 320c. The piezoelectric/electrostrictive element 320b is disposed on the middle line C of the vibrating plate 312. The piezoelectric/electrostrictive element 320a is connected to the drive part 342. The piezoelectric/electrostrictive element 320b and the piezoelectric/electrostrictive element 320c are connected to the voltage acquisition part 341.

According to the above-described construction, in the same manner as the construction shown in FIG. 14A or FIG. 14B, the acquisition of the resonant frequency through the application of the DC voltage, the acquisition of the resonant frequency through the application of the AC voltage, and the determination of the twisting mode are carried out. Specifically, for example, the detection of the bending mode is carried out by the output of the piezoelectric/electrostrictive element 320b, and the detection of the twisting mode is carried out by the output of the piezoelectric/electrostrictive element 320c. Consequently, it is possible to precisely carry out the determination of the vibration state of the vibrating plate 312.

Furthermore, according to the construction of this embodiment, the ratio of the resonant frequency in the bending mode and the twisting mode can be obtained through an experiment or a computer simulation such as a finite element method, and therefore, it is possible to calculate the resonant frequency of the bending mode from the resonant frequency of the twisting mode. Consequently, it is possible to detect the flight state of the micro drops using both the bending mode and the twisting mode.

Flight State Detection Apparatus According to Fourth Embodiment

Next, a fourth embodiment of the flight state detection apparatus according to the present invention will be described in detail with reference to FIGS. 15A to 15C.

Figure 15A:
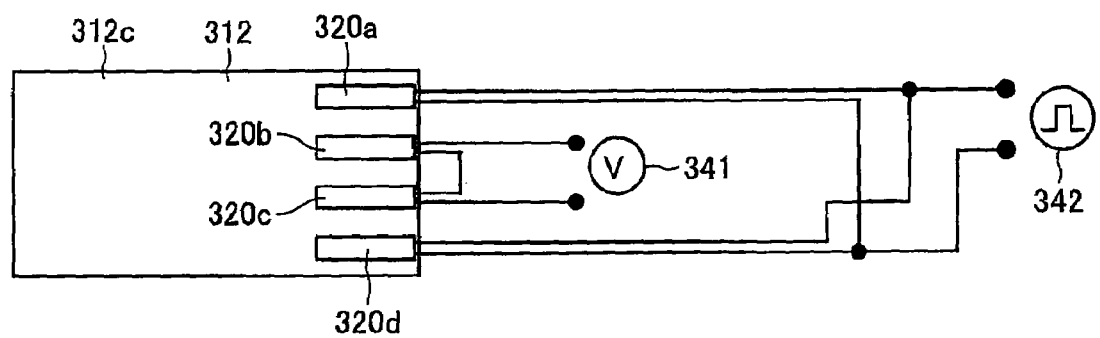
FIGS. 15A to 15C are enlarged views illustrating the construction of a fourth embodiment of the flight state detection apparatus shown in FIG. 8.

Referring to FIG. 15A, four piezoelectric/electrostrictive elements 320a to 320d are mounted at a single vibrating plate 312. The piezoelectric/electrostrictive element 320a and the piezoelectric/electrostrictive element 320d, which are symmetrically disposed along the lateral direction of the vibrating plate 312, are connected to the drive part 342. Also, the piezoelectric/electrostrictive element 320b and the piezoelectric/electrostrictive element 320c, which are symmetrically disposed along the lateral direction of the vibrating plate 312, are connected to the voltage acquisition part 341.

Figure 15B:
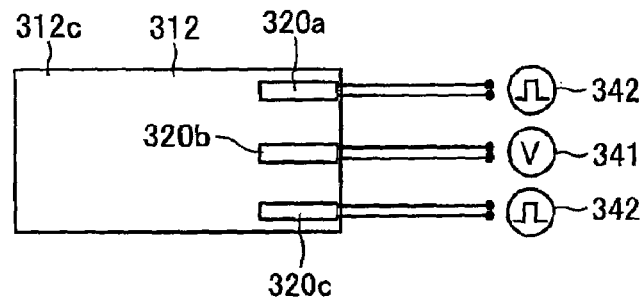

Referring to FIG. 15B, three piezoelectric/electrostrictive elements 320a to 320c are mounted at a single vibrating plate 312. The piezoelectric/electrostrictive element 320a and the piezoelectric/electrostrictive element 320c, which are symmetrically disposed along the lateral direction of the vibrating plate 312, are connected to the drive part 342. Also, the piezoelectric/electrostrictive element 320b, which is disposed at the middle of the vibrating plate 312 along the lateral direction of the vibrating plate 312, is connected to the voltage acquisition part 341.

Figure 15C:
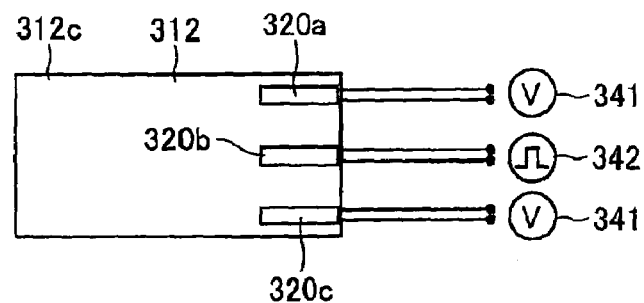

Referring to FIG. 15C, three piezoelectric/electrostrictive elements 320a to 320c are mounted at a single vibrating plate 312. The piezoelectric/electrostrictive element 320a and the piezoelectric/electrostrictive element 320c, which are symmetrically disposed along the lateral direction of the vibrating plate 312, are connected to the voltage acquisition part 341. Also, the piezoelectric/electrostrictive element 320b, which is disposed at the middle of the vibrating plate 312 along the lateral direction of the vibrating plate 312, is connected to the drive part 342.

That is to say, according to the constructions shown in FIGS. 15A to 15C, the voltage application or the electromotive measurement can be carried out with respect to the piezoelectric/electrostrictive elements symmetrically disposed along the lateral direction of the vibrating plate 312. Furthermore, in all cases, the respective piezoelectric/electrostrictive elements 320a, 320b . . . are disposed on the one-side surface of the vibrating plate 312 such that the directions of the piezoelectric/electrostrictive layers are the same.

According to the above-described construction, it is possible to forcibly vibrate the vibrating plate 312 in the primary bending mode and in the twisting mode by the combination in the connection of the respective piezoelectric/electrostrictive elements. Also, It is possible to acquire the resonant frequency in the primary bending mode and the twisting mode of the vibrating plate 312 by the combination in the connection of the respective piezoelectric/electrostrictive elements.

For example, in the case that the number of the piezoelectric/electrostrictive elements for applying the voltage is two (see FIG. 15A or FIG. 15B), the polarizing directions of the piezoelectric/electrostrictive layers of the two piezoelectric/electrostrictive elements are the same, the lower electrodes of the two piezoelectric/electrostrictive elements are grounded together, and AC voltages having the same phase are applied to the upper electrodes of the two piezoelectric/electrostrictive elements, whereby the vibration of the primary bending mode can be generated in the vibrating plate 312.

Also, in the case that the number of the piezoelectric/electrostrictive elements for applying the voltage is two (see FIG. 15A or FIG. 15B), the polarizing directions of the piezoelectric/electrostrictive layers of the two piezoelectric/electrostrictive elements are the same, the lower electrode of one of the piezoelectric/electrostrictive elements and the upper electrode of the other piezoelectric/electrostrictive element are grounded, and AC voltages having the same phase are applied to the remaining electrodes, whereby the vibration of the twisting mode can be generated in the vibrating plate 312.

Also, in the case that the number of the piezoelectric/electrostrictive elements for measuring the electromotive force is 2 (see FIG. 15A or FIG. 15C), the polarizing directions of the piezoelectric/electrostrictive layers of the two piezoelectric/electrostrictive elements are the same, the lower electrode of one of the piezoelectric/electrostrictive elements and the upper electrode of the other piezoelectric/electrostrictive element are grounded, and the electromotive force between the remaining electrodes of the two piezoelectric/electrostrictive elements is measured, whereby the resonant frequency of the vibration of the primary bending mode in the vibrating plate 312 can be acquired.

Also, in the case that the number of the piezoelectric/electrostrictive elements for measuring the electromotive force is 2 (see FIG. 15A or FIG. 15C), the polarizing directions of the piezoelectric/electrostrictive layers of the two piezoelectric/electrostrictive elements are the same, the lower electrodes of the two piezoelectric/electrostrictive elements are connected to each other, and the electromotive force between the upper electrodes of the two piezoelectric/electrostrictive elements is measured, whereby the resonant frequency of the vibration of the twisting mode in the vibrating plate 312 can be acquired.

Flight State Detection Apparatus According to Fifth Embodiment

Figure 16A:
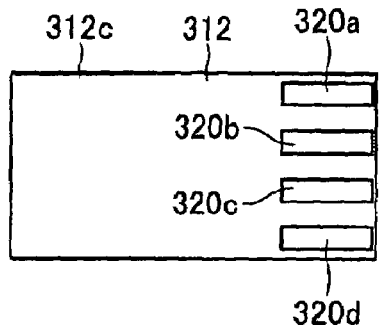
FIGS. 16A to 16C are enlarged views illustrating the construction of a fifth embodiment of the flight state detection apparatus shown in FIG. 8.
Figure 16B:
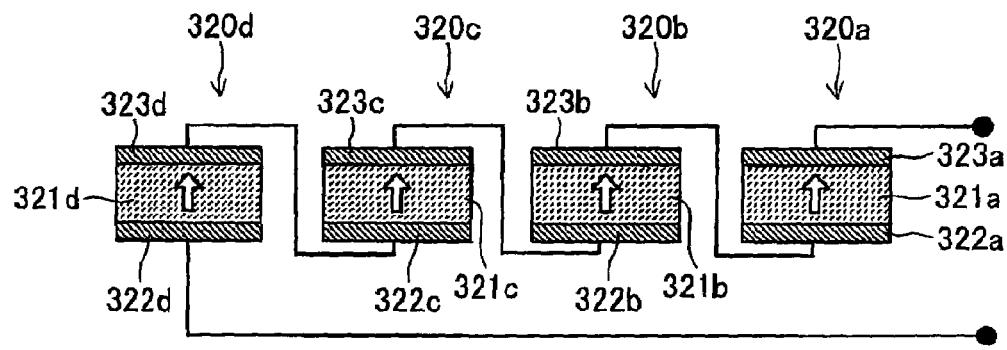
Figure 16C:
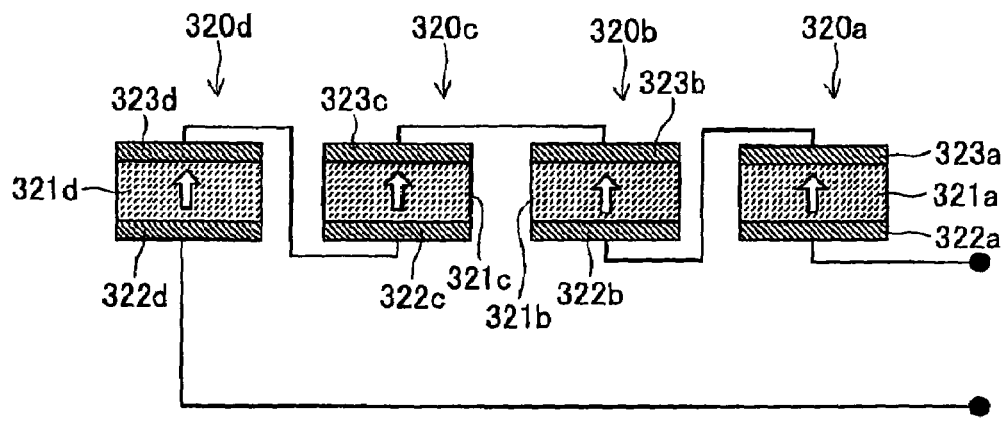

Next, a fifth embodiment of the flight state detection apparatus according to the present invention will be described in detail with reference to FIGS. 16A to 16C. FIG. 16A is a plan view illustrating the construction of this embodiment. FIGS. 16B and 16C are views illustrating the electrical connection of the piezoelectric/electrostrictive elements according to this embodiment.

According to this embodiment, as shown in FIG. 16A, four piezoelectric/electrostrictive elements 320a to 320d are mounted at a single vibrating plate 312 such that the piezoelectric/electrostrictive elements 320a to 320d are symmetrically disposed along the lateral direction of the vibrating plate 312. The piezoelectric/electrostrictive elements 320a to 320d may be connected to each other, for example, as shown in FIG. 16B or 16C.

The connection state shown in FIG. 16B is as follows. A lower electrode 322a of the piezoelectric/electrostrictive element 320a and an upper electrode 323b of the piezoelectric/electrostrictive element 320b are connected with each other. Also, a lower electrode 322b of the piezoelectric/electrostrictive element 320b and an upper electrode 323c of the piezoelectric/electrostrictive element 320c are connected with each other. Also, a lower electrode 322c of the piezoelectric/electrostrictive element 320c and an upper electrode 323d of the piezoelectric/electrostrictive element 320d are connected with each other. Between an upper electrode 323a of the piezoelectric/electrostrictive element 320a and a lower electrode 322d of the piezoelectric/electrostrictive element 320d is generated an output voltage corresponding to the vibration state. That is to say, all of the piezoelectric/electrostrictive elements 320a to 320d are directly electrically connected with each other.

The connection state shown in FIG. 16C is as follows. An upper electrode 323a of the piezoelectric/electrostrictive element 320a and a lower electrode 322b of the piezoelectric/electrostrictive element 320b are connected with each other. Also, a lower electrode 323d of the piezoelectric/electrostrictive element 320d and a lower electrode 322c of the piezoelectric/electrostrictive element 320c are connected with each other. That is to say, the piezoelectric/electrostrictive element 320a and the piezoelectric/electrostrictive element 320b are electrically connected with each other. Also, the piezoelectric/electrostrictive element 320c and the piezoelectric/electrostrictive element 320d are electrically connected with each other.

The one-side output terminal of the electrically connected piezoelectric/electrostrictive elements 320a and 320b is constructed from the upper electrode 323b of the piezoelectric/electrostrictive element 320b, and the other-side output terminal of the electrically connected piezoelectric/electrostrictive elements 320a and 320b is constructed from the lower electrode 322a of the piezoelectric/electrostrictive element 320a. Also, the one-side output terminal of the electrically connected piezoelectric/electrostrictive elements 320c and 320d is constructed from the upper electrode 323c of the piezoelectric/electrostrictive element 320c, and the other-side output terminal of the electrically connected piezoelectric/electrostrictive elements 320c and 320d is constructed from the lower electrode 322d of the piezoelectric/electrostrictive element 320d. The one-side output terminals are short-circuited with each other, and an output voltage corresponding to the vibration state is generated between the other-side output terminals.

Hereinafter, it is assumed that, when the micro drops of the sample solution collide with the target part 312c of the vibrating plate 312 according to the construction shown in FIG. 16A, one of the two vibration modes (the primary bending mode and the twisting mode) is realized, and, due to such vibration, an electromotive force having the following amplitudes is generated in the respective piezoelectric/electrostrictive elements 320a to 320d, for simplicity of the description of the operation.

Primary bending mode: V1, V1, V1, V1
Twisting mode: V1, 0.5V1, 0.5V1, V1

Specifically, In the case of the twisting mode, the electromotive force generated in the piezoelectric/electrostrictive elements 320a and 320d, which are located at opposite ends of the vibrating plate 312 in the lateral direction of the vibrating plate 312, is greater than the electromotive force generated in the piezoelectric/electrostrictive elements 320b and 320c, which are located closer to the middle of the vibrating plate 312 in the lateral direction of the vibrating plate 312.

In the connection state as shown in FIG. 16B, when the vibration of the complete primary bending mode is generated in the vibrating plate 312, the outputs of the respective piezoelectric/electrostrictive elements 320a, 320b, 320c, and 320d are added up. As a result, the total output of 4V1 is generated, and therefore, the output voltage generated by the vibration of the primary bending mode is increased. Consequently, even when super micro drops collide with the target part 312c, it is possible to detect the collision with high sensitivity.

Also, in the connection state as shown in FIG. 16B, electromotive forces ±V1 having the same absolute value and half-wavelength deviated phases are generated in the piezoelectric/electrostrictive elements 320a and 320d, which are symmetrically disposed in the lateral direction of the vibrating plate 312, due to the vibration of the twisting mode in the vibrating plate 312. Similarly, electromotive forces ±0.5V1 having the same absolute value and half-wavelength deviated phases are generated in the piezoelectric/electrostrictive elements 320b and 320c, which are symmetrically disposed in the lateral direction of the vibrating plate 312, due to the vibration of the twisting mode in the vibrating plate 312. When the outputs of the respective piezoelectric/electrostrictive elements 320a, 320b, 320c, and 320d are added up, the total output voltage becomes zero. That is to say, in the case that the vibration of the complete twisting mode is generated in the vibrating plate 312, the output voltage of the circuit shown in FIG. 16B becomes zero.

In the connection state as shown in FIG. 16C, an electromotive force of 2V1 is generated between the upper electrode 323b and the lower electrode 322a, i.e., the output terminals of the piezoelectric/electrostrictive elements 320a and 320b, which are electrically connected with each other, due to the vibration of the primary bending mode in the vibrating plate 312. Also, an electromotive force of 2V1 is generated between the upper electrode 323c and the lower electrode 322d, i.e., the output terminals of the piezoelectric/electrostrictive elements 320c and 320d, which are electrically connected with each other. The upper electrode 323b and the upper electrode 323c are short-circuited with each other. Consequently, in the case that the vibration of the complete primary bending mode is generated in the vibrating plate 312, the output voltage of the circuit shown in FIG. 16C becomes zero.

Also, in the connection state as shown in FIG. 16C, an electromotive force of +1.5V1 is generated between the upper electrode 323b and the lower electrode 322a, i.e., the output terminals of the piezoelectric/electrostrictive elements 320a and 320b, due to the vibration of the twisting mode in the vibrating plate 312. At the same time, an electromotive force of −1.5V1 is generated between the upper electrode 323c and the lower electrode 322d, i.e., the output terminals of the piezoelectric/electrostrictive elements 320c and 320d. Consequently, in the case that the vibration of the complete twisting mode is generated in the vibrating plate 312, the output voltage of the circuit shown in FIG. 16C becomes 3V1.

In this way, the detection of the flight state of the micro drops can be performed with higher sensitivity, and the determination of the vibration mode can be more easily performed by disposing the plural piezoelectric/electrostrictive elements 320a, 320b ... on the vibrating plate 312, and properly setting the electrical connection state therebetween.

Also, in this embodiment, the plural piezoelectric/electrostrictive elements 320a, 320b ... are electrically connected in series (not via the operation and control part 343 shown in FIG. 11), as such the circuits shown in FIGS. 16B and 16C are constructed. Consequently, according to this embodiment, the inner circuit construction of the operation and control part 343 shown in FIG. 11 is simplified, and therefore, the signal process performed by the operation and control part 343 is simplified.

Flight State Detection Apparatus According to Sixth Embodiment

Figure 17A:
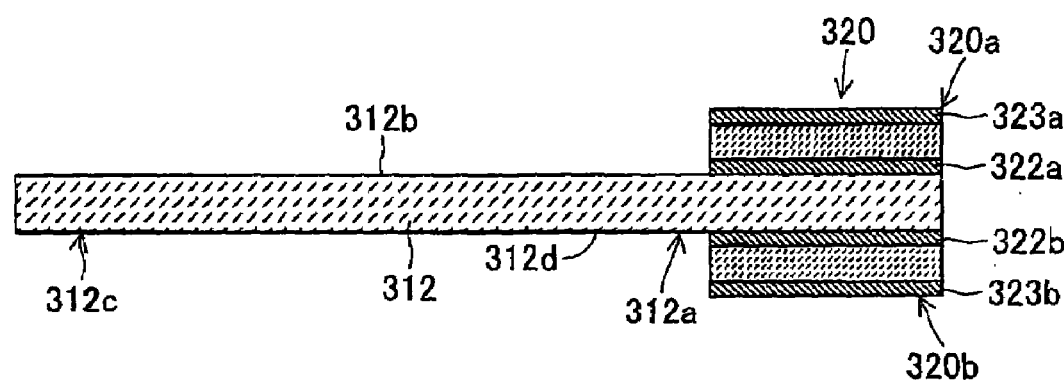
FIGS. 17A and 17B are enlarged views illustrating the construction of a sixth embodiment of the flight state detection apparatus shown in FIG. 8.
Figure 17B:
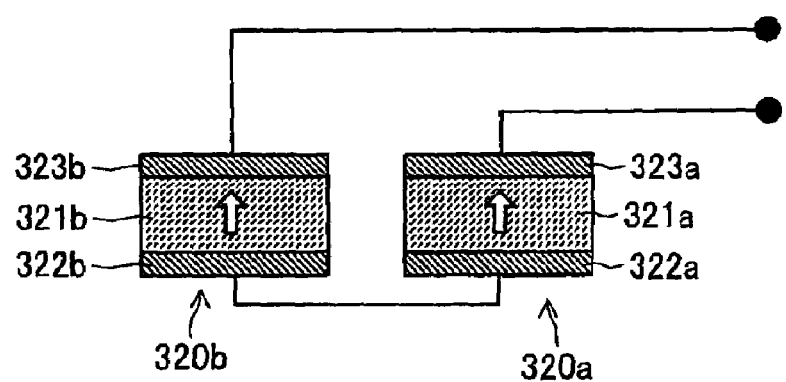

Next, a sixth embodiment of the flight state detection apparatus according to the present invention will be described in detail with reference to FIGS. 17A and 17B. FIG. 17A is an enlarged side sectional view illustrating the construction of this embodiment. FIG. 17B is a view illustrating the electrical connection of the piezoelectric/electrostrictive elements according to this embodiment.

In this embodiment, as shown in FIG. 17A, the piezoelectric/electrostrictive element 320a is mounted on the inside surface 312b of the detection part 312a of the vibrating plate 312. Also, the piezoelectric/electrostrictive element 320b is mounted on the outside surface 312d of the detection part 312a of the vibrating plate 312. That is to say, the piezoelectric/electrostrictive elements 320a and 320b are disposed on the opposite-side surfaces of the vibrating plate 312, respectively. Furthermore, the lower electrode 322b of the piezoelectric/electrostrictive element 320b disposed on the outside surface 312d of the vibrating plate 312 is the electrode disposed adjacent to the vibrating plate 312.

In this embodiment, as shown in FIG. 17B, the lower electrode 322a of the piezoelectric/electrostrictive element 320a and the lower electrode 322b of the piezoelectric/electrostrictive element 320b are short-circuited with each other. Between the upper electrode 323a of the piezoelectric/electrostrictive element 320a and the upper electrode 323b of the piezoelectric/electrostrictive element 320b is generated an output voltage corresponding to the vibration state.

According to the above-described construction, when vibration is generated in the vibrating plate 312, an electromotive force corresponding to the vibration state of the vibration plate 312 is generated in the piezoelectric/electrostrictive element 320a on the inside surface 312b of the vibrating plate 312 and the piezoelectric/electrostrictive element 320b on the outside surface 312d of the vibrating plate 312. In the case that the target part 312c of the vibrating plate 312 is displaced downward in the drawing, for example, a tensile stress is generated in the piezoelectric/electrostrictive layer 321a of the piezoelectric/electrostrictive element 320a, and a compressive stress is generated in the piezoelectric/electrostrictive layer 321b of the piezoelectric/electrostrictive element 320b. As a result, waveforms of electromotive forces having almost the same absolute value and half-wavelength deviated phases are generated in the piezoelectric/electrostrictive element 320a on the inside surface 312b of the vibrating plate 312 and the piezoelectric/electrostrictive element 320b on the outside surface 312d of the vibrating plate 312. The output of the circuit shown in FIG. 17B is double the output for the case that only the piezoelectric/electrostrictive element 320a is provided (the case that the piezoelectric/electrostrictive element 320b is not provided). Consequently, even when super micro drops collide with the target part 312c, it is possible to detect the collision with high sensitivity.

Flight State Detection Apparatus According to Seventh Embodiment

Figure 18A:
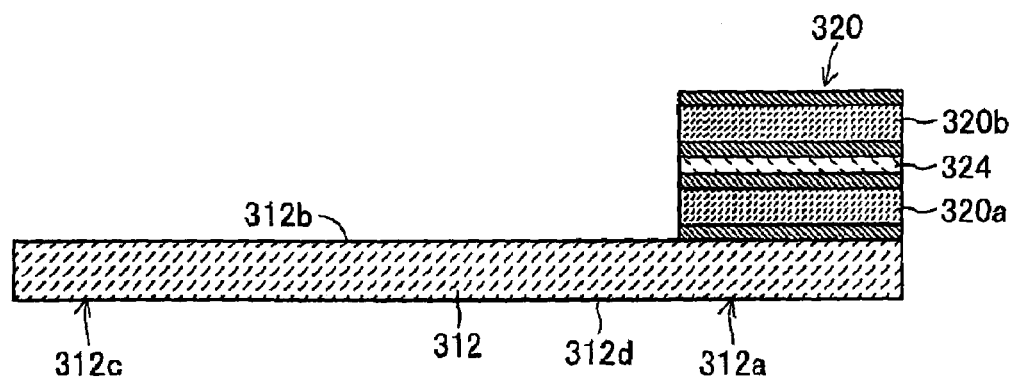
FIGS. 18A and 18B are enlarged views illustrating the construction of a seventh embodiment of the flight state detection apparatus shown in FIG. 8.
Figure 18B:
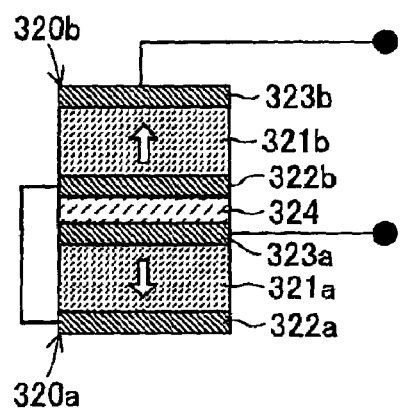

Next, a seventh embodiment of the flight state detection apparatus according to the present invention will be described in detail with reference to FIGS. 18A and 18B. FIG. 18A is an enlarged side sectional view illustrating the construction of this embodiment. FIG. 18B is a view illustrating the electrical connection of the piezoelectric/electrostrictive elements according to this embodiment.

In this embodiment, as shown in FIG. 18A, the piezoelectric/electrostrictive element 320a is mounted on the inside surface 312b of the detection part 312a of the vibrating plate 312. Also, the piezoelectric/electrostrictive element 320b is disposed above the piezoelectric/electrostrictive element 320a while an insulation layer 324 is interposed between the piezoelectric/electrostrictive elements 320a and 320b. The piezoelectric/electrostrictive element 320a, the insulation layer 324, and the piezoelectric/electrostrictive element 320b are integrally formed to constitute a single body by sintering.

In this embodiment, as shown in FIG. 18B, the piezoelectric/electrostrictive elements 320a and 320b are constructed such that the polarizing direction of the piezoelectric/electrostrictive layer 321a of the piezoelectric/electrostrictive element 320a is opposite to the polarizing direction of the piezoelectric/electrostrictive layer 321b of the piezoelectric/electrostrictive element 320b. The lower electrode 322a of the piezoelectric/electrostrictive element 320a and the lower electrode 322b of the piezoelectric/electrostrictive element 320b are short-circuited with each other. Between the upper electrode 323a of the piezoelectric/electrostrictive element 320a and the upper electrode 323b of the piezoelectric/electrostrictive element 320b is generated an output voltage corresponding to the vibration state. That is to say, the piezoelectric/electrostrictive element 320a and the piezoelectric/electrostrictive element 320b are electrically connected with each other.

According to the above-described construction, the output of the circuit shown in FIG. 18B is double the output for the case that only the piezoelectric/electrostrictive element 320a is provided (the case that the piezoelectric/electrostrictive element 320b is not provided). Consequently, even when super micro drops collide with the target part 312c, it is possible to detect the collision with high sensitivity.

<Suggestion of Modifications>

The above-described embodiments have been disclosed merely to illustrate representative embodiments of the present invention considered as the most preferred embodiments at the time of filing of the present application. Consequently, the present invention is not limited to the above-described embodiments, and it is appreciated that various modifications are possible without changing essential parts of the present invention.

Hereinafter, a few modifications will be illustrated within the limits of addition possible at the time of filing of the present application (as far as time is allowed) under the first-to-file rule. However, it is not necessary to mention that the present invention is also not limited to these modifications. Limiting the present invention based on the disclosures of the embodiments described above and the modifications described below (especially, limiting the respective components constituting the means to solve the problems of the present invention, particularly, the components which are expressed operatively and functionally, based on the description of the preferred embodiments) is not allowed because the limitation trespasses on benefits of the applicant who has hastened to file the application under the first-to-file rule, the limitation provides imitators with undue profits, and therefore, the limitation is opposed to the purpose of the patent law prescribing the protection and utilization of the invention. Furthermore, it is not necessary to mention that the following modifications can be appropriately combined with each other within the scope of consistency.

(i) The present invention is not limited to the detection of the flight state of the micro drops ejected by the micropipettes as disclosed from the above-described embodiments. Also, the micro object, the flight state of which is detected according to the present invention, is not limited to the micro drops. Also, the flight direction of the micro object is not limited to the vertically-downward direction. Furthermore, in the electric signal processing carried out when detecting the flight state of the micro object, electric current, frequency, phase, etc. may be used in addition to the voltage used in the above-described embodiments.

(ii) For example, the aperture plate 330 may be omitted from FIGS. 9A to 9C. Also, the coating layer 313 may be omitted from FIGS. 9A to 9C. Furthermore, the coating layer 313 may be formed using a thin film forming method, such as deposition in addition to a thick film forming method, such as paste application or screen printing. Moreover, the entire inside surface 312b of the vibrating plate 312 may be covered with the coating layer 313.

(iii) The piezoelectric/electrostrictive element 320 (320a . . . ) constructed as shown in FIGS. 9 to 16 may have the opposite-side construction as shown in FIGS. 17A and 17B or the multi-layer construction as shown in FIGS. 18A and 18B. Of course, it is possible that the piezoelectric/electrostrictive element has the opposite-side and multi-layer construction.

(iv) In FIGS. 16 to 18, the number and the polarizing directions of the piezoelectric/electrostrictive elements, and the connection between the electrodes may be arbitrarily changed. The connection between the respective piezoelectric/electrostrictive elements 320a, 320b . . . may be directly accomplished using wiring pattern. Alternatively, it is possible that the respective piezoelectric/electrostrictive elements 320a, 320b . . . are individually connected to the voltage acquisition part 341 (see FIG. 11), and the respective piezoelectric/electrostrictive elements 320a, 320b . . . are substantially electrically connected to each other by the signal processing of the operation and control part 343.

(v) In FIGS. 18A and 18B, it is possible that the polarizing direction of the piezoelectric/electrostrictive layer 321a of piezoelectric/electrostrictive element 320a and the polarizing direction of the piezoelectric/electrostrictive layer 321b of piezoelectric/electrostrictive element 320b are the same. In this case, it is also possible that the insulation layer 324 is omitted, and the upper electrode 323a of the piezoelectric/electrostrictive element 320a and the lower electrode 322b of the piezoelectric/electrostrictive element 320b are integrally formed to constitute a single body, whereby voltage corresponding to the vibration state is generated between the lower electrode 322a of the piezoelectric/electrostrictive element 320a and the upper electrode 323b of the piezoelectric/electrostrictive element 320b.

Figure 19:
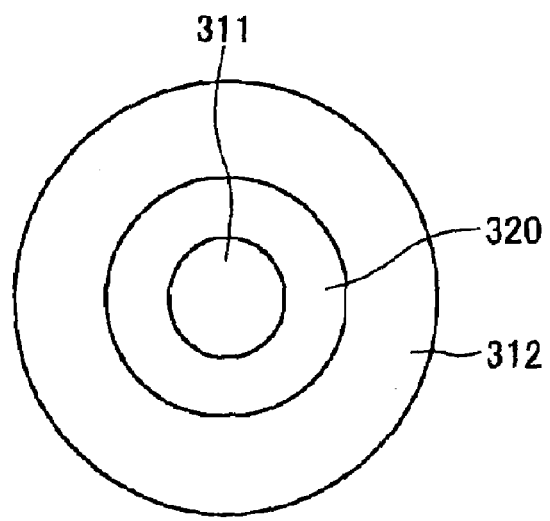
FIG. 19 is an enlarged plan view illustrating a modification of the flight state detection apparatus shown in FIGS. 9 to 18.

(vi) As shown in FIG. 19, the vibrating plate 312 may be formed in the shape of a disk. In this case, the thick support part 311 is formed in the shape of a disk having a radius smaller than that of the vibrating plate 312, and the thick support part is disposed approximately at the middle of the vibrating plate 312. Also, the piezoelectric/electrostrictive element 320 is formed approximately in the plan-view shape of a donut.

Figure 20:
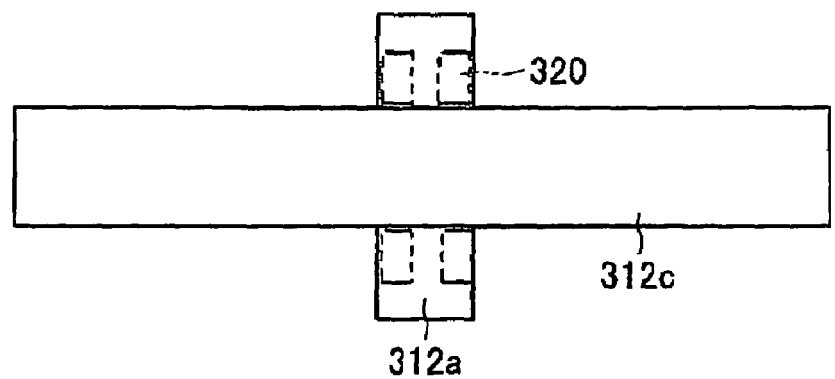
FIG. 20 is an enlarged plan view illustrating another modification of the flight state detection apparatus shown in FIGS. 9 to 18.

(vii) As shown in FIG. 20, it is possible that the detection part 312a and the target part 312c are constructed from a rectangular plate-shaped member, and the target part 312c is disposed about the central axis of the detection part 312a in the longitudinal direction of the detection part 312a in the shape of a seesaw.

Figure 21A:
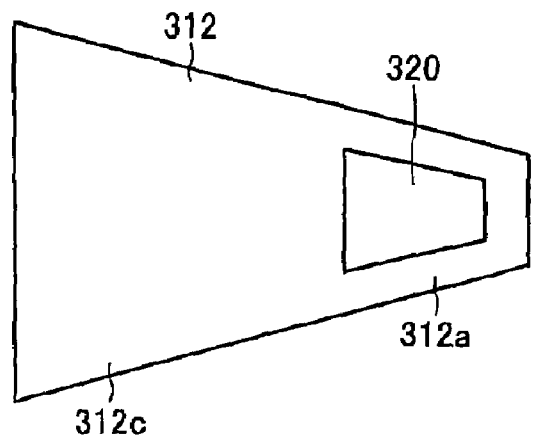
FIGS. 21A to 21C are enlarged views illustrating a modification of the flight state detection apparatus shown in FIGS. 9 to 18.
Figure 21B:
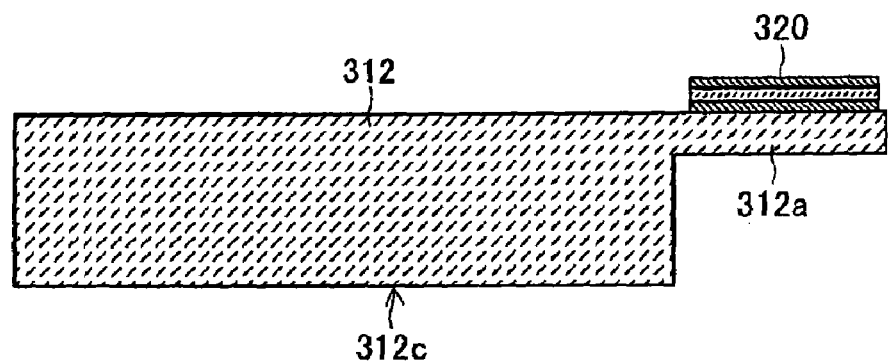
Figure 21C:
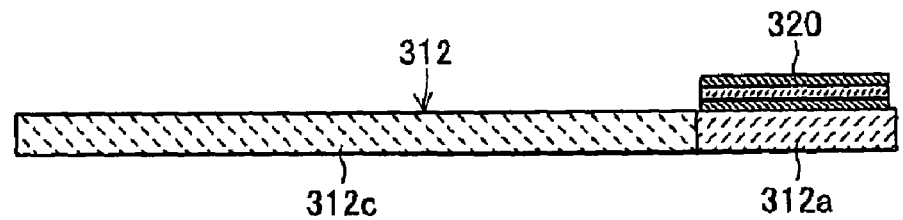

(viii) As shown in FIGS. 21A to 21C, the vibrating plate 312 may have various constructions so long as stress can be concentrated upon the detection part 312a.

For example, as shown in FIG. 21A, the vibrating plate 312 may be formed such that the width of the vibrating plate 312 is gradually decreased from the target part 312c to the detection part 312a.

Also, as shown in FIG. 21B, the vibrating plate 312 may be formed such that the thickness of the detection part 312a is less than that of the other parts of the vibrating plate 312. According to this construction, in the case that micro drops collide with the target part 312c, the parts including the target part 312c (the parts excluding the detection part 312a) are not bent at all. Also, the mass of the parts including the target part 312c is very large as compared to that of the detection part 312a.

Consequently, according to the construction shown in FIG. 21B, when a micro object collides with the target part 312c, stress is efficiently generated in the detection part 312a due to the influence of the collision. Also, even when foreign matter is attached to the target part 312c of the vibrating plate 312, it is possible to control the vibration plate 312 such that the shift of the resonant frequency of the vibrating plate 312 is small.

Furthermore, as shown in FIG. 21C, it is possible to obtain the same operation and effect as the case of the FIG. 21B by adjusting the coefficient of elasticity of the detection part 312a such that the coefficient of elasticity of the detection part 312a is less than those of the other parts of the vibrating plate 312. Also, as shown in FIG. 21C, the width of the vibrating plate 312 may be uniform, or, as shown in FIGS. 10B and 21A, the vibrating plate 312 may be formed such that the width of the detection part 312a is less than those of the other parts of the vibrating plate 312. Furthermore, as shown in FIG. 21B, the thickness of the vibrating plate 312 may be formed such that the thickness of the detection part 312a is less than those of the other parts of the vibrating plate 312.

Figure 22:
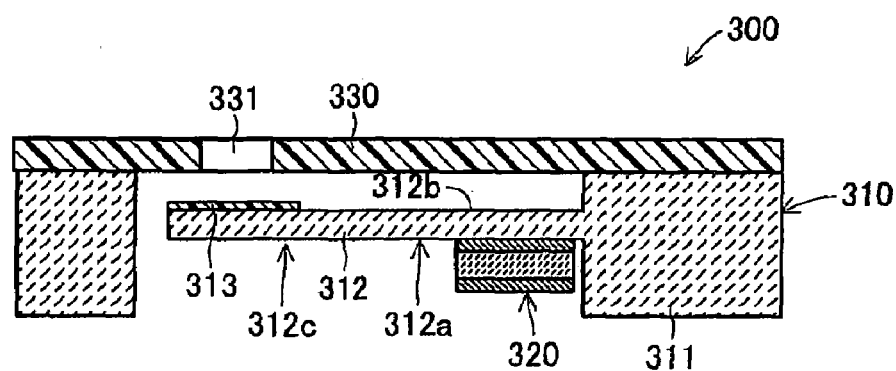
FIG. 22 is an enlarged sectional view illustrating a modification of the flight state detection apparatus shown in FIGS. 9 to 18.

(ix) As shown in FIG. 22, it is possible that the piezoelectric/electrostrictive element 320 is formed at the inner part of the inside surface 312b of the vibrating plate 312.

Figure 23A:
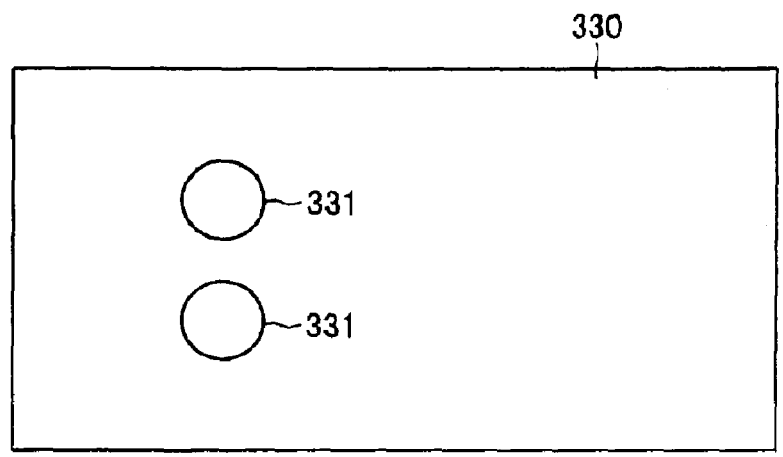
FIGS. 23A and 23B are enlarged plan views illustrating a modification of the flight state detection apparatus shown in FIGS. 9 to 18.
Figure 23B:
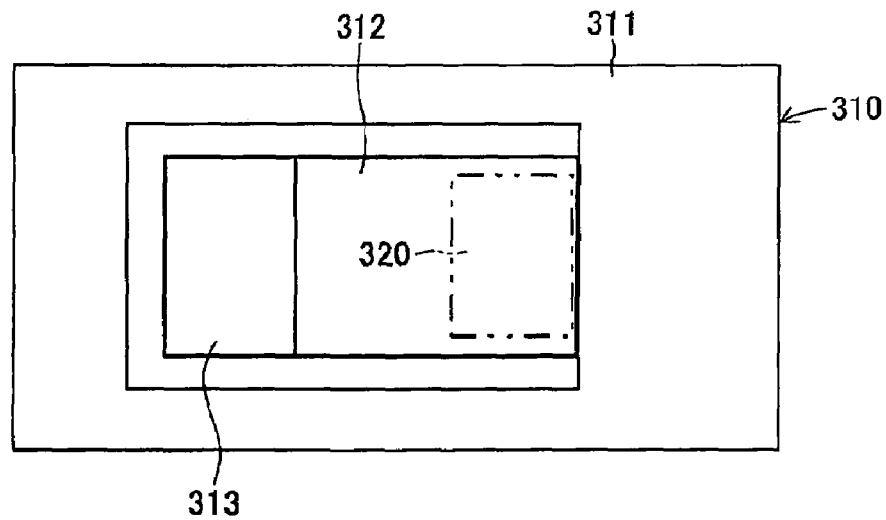

(x) The width of the vibrating plate 312 may be set such that, as shown in FIG. 23A, plural apertures 331 may be formed in the aperture plate 330, and, as shown in FIG. 23B, micro objects having passed through the apertures 331 simultaneously collide with the vibrating plate 312. Furthermore, as shown in FIG. 23B, the aperture plate 330 shown in FIG. 23A may be omitted.

(xi) In the construction shown in FIGS. 9 to 23, the vibrating plate 312 may be disposed such that the vibrating plate 312 (the sensor substrate 310) intersect the horizontal plane, and therefore, the free end side of the vibrating plate 312 (the target part 312c and the coating layer 313 side) is lower than the fixed end side of the vibrating plate 312 (the detection part 312a side). Consequently, it is possible that spray of the micro drops of the sample solution colliding with the vibrating plate 312 (the target part 312c and the coating layer 313) is ejected downward from the vibrating plate 312 due to gravity.

(Xii) In addition, the respective components constituting the means to solve the problems of the present invention, particularly, the components which are expressed operatively and functionally, include all structures that can be operatively and functionally realized in addition to the clearly defined structures disclosed in the above-described embodiments and modifications.

As apparent from the above description, the flight state detection apparatus and the flight state detection method according to the present invention can detect the flight state of the micro object colliding with the target part only by disposing the target part on the flight route of the micro object in flight and detecting the collision state between the micro object and the target part using the piezoelectric/electrostrictive element. That is to say, according to the present invention, it is possible to accurately detect the flight state of the micro object ejected from the micro object ejection apparatus (the ejection state of the micro object ejection apparatus) through the use of the flight state detection apparatus, which is manufactured in a simplified structure and at low costs.

What is claimed is:

1. A flight state detection apparatus capable of detecting the flight state of a micro object in flight, the flight state detection apparatus comprising:

a vibration generating part including a solid thin plate target part having a water repellent coating layer thereon, with which the micro object collides, the vibration generating part being constructed such that vibration is generated in the vibration generating part by the collision of the micro object with the water repellent coating layer on the target part; and a piezoelectric/electrostrictive element constructed to convert the vibration generated in the vibration generating part into an electric signal.

2. The flight state detection apparatus according to claim 1, further comprising:

a flat plate-shaped aperture plate located at an upper stream side higher than the target part in a flight direction of the micro object, the aperture plate intersecting the flight direction, wherein the aperture plate is provided with an aperture, which is a through-hole for allowing the micro object to pass therethrough.

3. The flight state detection apparatus according to claim 2, further comprising:

a drive part for generating a drive voltage necessary to drive the piezoelectric/electrostrictive element.

4. The flight state detection apparatus according to claim 3, further comprising:

a resonant frequency acquisition part for acquiring a resonant frequency of the vibration generating part, wherein the drive part is constructed such that the drive part drives the piezoelectric/electrostrictive element based on the resonant frequency acquired by the resonant frequency acquisition part.

5. The flight state detection apparatus according to claim 4, wherein the resonant frequency acquisition part is constructed such that the resonant frequency acquisition part acquires the resonant frequency after output of the drive voltage from the drive part is interrupted.

6. The flight state detection apparatus according to claim 5, further comprising:

a vibration mode determining part for determining a vibration mode of the vibration generating part based on the electric signal.

7. The flight state detection apparatus according to claim 6, wherein a plurality of the target parts are mounted to the single vibration generating part.

8. The flight state detection apparatus according to claim 7, wherein a plurality of the piezoelectric/electrostrictive elements are electrically connected with each other.

9. The flight state detection apparatus according to claim 8, wherein the vibration generating part is constructed from a plate-shaped member having a longitudinal direction, the target part comprises one end side of the plate-shaped member in the longitudinal direction of the plate-shaped member, and the piezoelectric/electrostrictive element is fixedly mounted on a surface of the other end side of the plate-shaped member, which is opposite to the one end side of the plate-shaped member.

10. The flight state detection apparatus according to claim 9, wherein the plate-shaped member is constructed such that the rigidity of the other end side of the plate-shaped member is lower than that of the one end side of the plate-shaped member.

11. The flight state detection apparatus according to claim 10, wherein the plurality of piezoelectric/electrostrictive elements are fixedly mounted on one-side surface of the plate-shaped member and on a predetermined position of the other-side surface of the plate-shaped member, which is opposite to an inner part of the one-side surface of the plate-shaped member.

12. The flight state detection apparatus according to claim 4, wherein the drive part is constructed such that the drive part outputs the drive voltage with respect to a plurality of piezoelectric/electrostrictive elements, and the resonant frequency acquisition part is constructed such that the resonant frequency acquisition part acquires the resonant frequency based on electric signals from piezoelectric/electrostrictive elements other than the piezoelectric/electrostrictive elements to which the drive voltage from the drive part is outputted.

13. The flight state detection apparatus according to claim 12, further comprising:

a vibration mode determining part for determining a vibration mode of the vibration generating part based on the electric signal.

14. The flight state detection apparatus according to claim 13, wherein a plurality of the target parts are mounted to the single vibration generating part.

15. The flight state detection apparatus according to claim 14, wherein a plurality of the piezoelectric/electrostrictive elements are electrically connected with each other.

16. The flight state detection apparatus according to claim 15, wherein the vibration generating part is constructed from a plate-shaped member having a longitudinal direction, the target part comprises one end side of the plate-shaped member in the longitudinal direction of the plate-shaped member, and the piezoelectric/electrostrictive element is fixedly mounted on a surface of the other end side of the plate-shaped member, which is opposite to the one end side of the plate-shaped member.

17. The flight state detection apparatus according to claim 16, wherein the plate-shaped member is constructed such that the rigidity of the other end side of the plate-shaped member is lower than that of the one end side of the plate-shaped member.

18. The flight state detection apparatus according to claim 17, wherein the plurality of piezoelectric/electrostrictive elements are fixedly mounted on one-side surface of the plate-shaped member and on a predetermined position of the other-side surface of the plate-shaped member, which is opposite to an inner part of the one-side surface of the plate-shaped member.

19. A flight state detection apparatus capable of detecting the flight state of a micro object in flight, the flight state detection apparatus comprising:

a vibration generating part having a target part, with which the micro object collides, the vibration generating part being constructed such that vibration is generated in the vibration generating part by the collision of the micro object with the target part;

a piezoelectric/electrostrictive element constructed to convert the vibration generated in the vibration generating part into an electric signal;

a micro object ejection part constructed to eject the micro object; and a control part for controlling the micro object ejection part such that the micro object can be ejected at a specific frequency approximate to 1/n times (n is a natural number) a resonant frequency of the vibration generating part.

20. The flight state detection apparatus according to claim 19,
wherein on the assumption that the resonant frequency is f0 and the specific frequency is f1,
the control part controls the micro object ejection part such that the micro object is ejected at the specific frequency satisfying the following inequality:

$(n-0.2)f1 \leq f0 \leq (n+0.25)f1$ [n is a natural number].

21. The flight state detection apparatus according to claim 20,
wherein on the assumption that time necessary for the vibration generating part to absorb kinetic energy of the micro object when the micro object collides with the target part is T1, and an inherent period corresponding to the resonant frequency of the vibration generating part is T0,
the control part controls the micro object ejection part such that the micro object is ejected under the condition satisfying the following inequality: $T1 \leq 0.2\ T0$.

22. The flight state detection apparatus according to claim 21, further comprising:
a drive part for generating a drive voltage necessary to drive the piezoelectric/electrostrictive element.

23. The flight state detection apparatus according to claim 22, further comprising:
a resonant frequency acquisition part for acquiring a resonant frequency of the vibration generating part,
wherein the drive part is constructed such that the drive part drives the piezoelectric/electrostrictive element based on the resonant frequency acquired by the resonant frequency acquisition part.

24. The flight state detection apparatus according to claim 23, wherein the resonant frequency acquisition part is constructed such that the resonant frequency acquisition part acquires the resonant frequency after output of the drive voltage from the drive part is interrupted.

25. The flight state detection apparatus according to claim 24, further comprising:
a vibration mode determining part for determining a vibration mode of the vibration generating part based on the electric signal.

26. The flight state detection apparatus according to claim 25, further comprising:
a coating layer formed at a surface of the target part.

27. The flight state detection apparatus according to claim 26, wherein a plurality of the target parts are mounted to the single vibration generating part.

28. The flight state detection apparatus according to claim 27, wherein a plurality of the piezoelectric/electrostrictive elements are electrically connected with each other.

29. The flight state detection apparatus according to claim 28,
wherein the vibration generating part is constructed from a plate-shaped member having a longitudinal direction,
the target part is mounted at one end side of the plate-shaped member in the longitudinal direction of the plate-shaped member, and
the piezoelectric/electrostrictive element is fixedly mounted on a surface of the other end side of the plate-shaped member, which is opposite to the one end side of the plate-shaped member.

30. The flight state detection apparatus according to claim 29, wherein the plate-shaped member is constructed such that the rigidity of the other end side of the plate-shaped member is lower than that of the one end side of the plate-shaped member.

31. The flight state detection apparatus according to claim 30, wherein the plurality of piezoelectric/electrostrictive elements are fixedly mounted on one-side surface of the plate-shaped member and on a predetermined position of the other-side surface of the plate-shaped member, which is opposite to an inner part of the one-side surface of the plate-shaped member.

32. The flight state detection apparatus according to claim 23,
wherein the drive part is constructed such that the drive part outputs the drive voltage with respect to some of the plurality of piezoelectric/electrostrictive elements, and
the resonant frequency acquisition part is constructed such that the resonant frequency acquisition part acquires the resonant frequency based on the electric signals from the other piezoelectric/electrostrictive elements than the piezoelectric/electrostrictive elements to which the drive voltage from the drive part is outputted.

33. The flight state detection apparatus according to claim 32, further comprising:
a vibration mode determining part for determining a vibration mode of the vibration generating part based on the electric signal.

34. The flight state detection apparatus according to claim 33, further comprising:
a coating layer formed at a surface of the target part.

35. The flight state detection apparatus according to claim 34, wherein a plurality of the target parts are mounted to the single vibration generating part.

36. The flight state detection apparatus according to claim 35, wherein a plurality of the piezoelectric/electrostrictive elements are electrically connected with each other.

37. The flight state detection apparatus according to claim 36,
wherein the vibration generating part is constructed from a plate-shaped member having a longitudinal direction,
the target part is mounted at one end side of the plate-shaped member in the longitudinal direction of the plate-shaped member, and
the piezoelectric/electrostrictive element is fixedly mounted on a surface of the other end side of the plate-shaped member, which is opposite to the one end side of the plate-shaped member.

38. The flight state detection apparatus according to claim 37, wherein the plate-shaped member is constructed such that the rigidity of the other end side of the plate-shaped member is lower than that of the one end side of the plate-shaped member.

39. The flight state detection apparatus according to claim 38, wherein the plurality of piezoelectric/electrostrictive elements are fixedly mounted on one-side surface of the plate-shaped member and on a predetermined position of the other-side surface of the plate-shaped member, which is opposite to an inner part of the one-side surface of the plate-shaped member.

40. A flight state detection method of detecting the flight state of a micro object ejected from a micro object ejection part, the flight state detection method comprising the steps of:
ejecting the micro object from the micro object ejection part;
forcing the ejected micro object to collide with a target part to vibrate a vibration generating part having the target part;
converting the vibration of the vibration generating part into an electric signal using a piezoelectric/electrostrictive element; and detecting the flight state of the micro object based on the electric signal.

41. The flight state detection method according to claim 40, wherein the step of ejecting the micro object includes ejecting the micro object at a specific frequency approximate to 1/n times (n is a natural number) a resonant frequency of the vibration generating part.

42. The flight state detection method according to claim 41, wherein on the assumption that the resonant frequency is f0 and the specific frequency is f1,
the step of ejecting the micro object includes ejecting the micro object at the specific frequency satisfying the following inequality:

$(n-0.2)f1 \leq f0 \leq (n+0.25)f1$ [n is a natural number].

43. The flight state detection method according to claim 42, wherein on the assumption that time necessary for the vibration generating part to absorb kinetic energy of the micro object when the micro object collides with the target part is T1, and an inherent period corresponding to the resonant frequency of the vibration generating part is T0,
the step of ejecting the micro object includes ejecting the micro object under the condition satisfying the following inequality:

$T1 \leq 0.2\ T0$.

44. The flight state detection method according to claim 43, wherein the step of detecting the flight state of the micro object includes determining a vibration mode of the vibration generating part based on the electric signal.

45. The flight state detection method according to claim 44, wherein the step of detecting the flight state of the micro object includes determining the vibration mode of the vibration generating part based on electric signals outputted from a first piezoelectric/electrostrictive element and a second piezoelectric/electrostrictive element, which are electrically connected with each other.

46. The flight state detection method according to claim 45, further comprising the steps of:
acquiring the resonant frequency of the vibration generating part; and
driving the piezoelectric/electrostrictive element(s) based on the acquired resonant frequency.

47. The flight state detection method according to claim 46, wherein the step of acquiring the resonant frequency of the vibration generating part is carried out after the step of driving the piezoelectric/electrostrictive element(s) is completed.

48. The flight state detection method according to claim 47, wherein
the step of driving the piezoelectric/electrostrictive element(s) includes outputting the drive voltage with respect to some of the plurality of piezoelectric/electrostrictive elements, and
the step of acquiring the resonant frequency of the vibration generating part includes acquiring the resonant frequency based on the electric signals from the other piezoelectric/electrostrictive elements than the piezoelectric/electrostrictive elements to which the drive voltage is outputted.

49. The flight state detection method according to claim 48, wherein the step of ejecting the micro object includes forcing the micro object to collide with a predetermined position of the target part at a predetermined frequency to vibrate the vibration generating part in a predetermined vibration mode.

50. The flight state detection method according to claim 40, wherein the step of detecting the flight state of the micro object includes determining a vibration mode of the vibration generating part based on the electric signal.

51. The flight state detection method according to claim 50, wherein the step of detecting the flight state of the micro object includes determining the vibration mode of the vibration generating part based on electric signals outputted from a first piezoelectric/electrostrictive element and a second piezoelectric/electrostrictive element, which are electrically connected with each other.

52. The flight state detection method according to claim 51, further comprising the steps of:
acquiring the resonant frequency of the vibration generating part; and
driving the piezoelectric/electrostrictive element(s) based on the acquired resonant frequency.

53. The flight state detection method according to claim 52, wherein the step of acquiring the resonant frequency of the vibration generating part is carried out after the step of driving the piezoelectric/electrostrictive element(s) is completed.

54. The flight state detection method according to claim 53, wherein
the step of driving the piezoelectric/electrostrictive element(s) includes outputting the drive voltage with respect to some of the plurality of piezoelectric/electrostrictive elements, and
the step of acquiring the resonant frequency of the vibration generating part includes acquiring the resonant frequency based on the electric signals from the other piezoelectric/electrostrictive elements than the piezoelectric/electrostrictive elements to which the drive voltage is outputted.

55. The flight state detection method according to claim 54, wherein the step of ejecting the micro object includes forcing the micro object to collide with a predetermined position of the target part at a predetermined frequency to vibrate the vibration generating part in a predetermined vibration mode.

56. The flight state detection method according to claim 40, further comprising the steps of:
acquiring the resonant frequency of the vibration generating part; and
driving the piezoelectric/electrostrictive element(s) based on the acquired resonant frequency.

57. The flight state detection method according to claim 56, wherein the step of acquiring the resonant frequency of the vibration generating part is carried out after the step of driving the piezoelectric/electrostrictive element(s) is completed.

58. The flight state detection method according to claim 57, wherein
the step of driving the piezoelectric/electrostrictive element(s) includes outputting the drive voltage with respect to some of the plurality of piezoelectric/electrostrictive elements, and
the step of acquiring the resonant frequency of the vibration generating part includes acquiring the resonant frequency based on the electric signals from the other piezoelectric/electrostrictive elements than the piezoelectric/electrostrictive elements to which the drive voltage is outputted.

59. The flight state detection method according to claim 58, wherein the step of ejecting the micro object includes forcing the micro object to collide with a predetermined position of the target part at a predetermined frequency to vibrate the vibration generating part in a predetermined vibration mode.

60. A flight state detection apparatus capable of detecting the flight state of a micro object in flight, the flight state detection apparatus comprising:

a vibration generating part having a target part, with which the micro object collides, the vibration generating part being constructed such that vibration is generated in the vibration generating part by the collision of the micro object with the target part;

a flat plate-shaped aperture plate located at an upper stream side higher than the target part in a flight direction of the micro object, the aperture plate intersecting the flight direction, wherein the aperture plate is provided with an aperture, which is a through-hole for allowing the micro object to pass therethrough;

a piezoelectric/electrostrictive element constructed to convert the vibration generated in the vibration generating part into an electric signal;

a drive part for generating a drive voltage necessary to drive the piezoelectric/electrostrictive element; and a resonant frequency acquisition part for acquiring a resonant frequency of the vibration generating part after output of the drive voltage from the drive part is interrupted, wherein the drive part drives the piezoelectric/electrostrictive element based on the resonant frequency acquired by the resonant frequency acquisition part.

61. A flight state detection apparatus capable of detecting the flight state of a micro object in flight, the flight state detection apparatus comprising:

a vibration generating part having a target part, with which the micro object collides, the vibration generating part being constructed such that vibration is generated in the vibration generating part by the collision of the micro object with the target part;

a flat plate-shaped aperture plate located at an upper stream side higher than the target part in a flight direction of the micro object, the aperture plate intersecting the flight direction, wherein the aperture plate is provided with an aperture, which is a through-hole for allowing the micro object to pass therethrough;

a plurality of piezoelectric/electrostrictive elements, at least some of which are constructed to convert the vibration generated in the vibration generating part into an electric signal;

a drive part for generating a drive voltage necessary to drive at least some of the piezoelectric/electrostrictive elements; and a resonant frequency acquisition part for acquiring a resonant frequency of the vibration generating part, wherein the drive part outputs the drive voltage with respect to some of the plurality of piezoelectric/electrostrictive elements, and the resonant frequency acquisition part acquires the resonant frequency based on the electric signals from the piezoelectric/electrostrictive elements other than the piezoelectric/electrostrictive elements to which the drive voltage from the drive part is outputted.

* * * * *